US010935540B2

(12) United States Patent
Guerreiro et al.

(10) Patent No.: US 10,935,540 B2
(45) Date of Patent: Mar. 2, 2021

(54) GDF-15 AS A HAEMATOLOGICAL TOXICITY BIOMARKER

(71) Applicants: Novartis AG, Basel (CH); Nelson Guerreiro, Basel (CH); Christophe Meille, Sierentz (FR); Jens Wuerthner, Steinen (DE)

(72) Inventors: Nelson Guerreiro, Basel (CH); Christophe Meille, Sierentz (FR); Jens Wuerthner, Steinen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/749,544

(22) PCT Filed: Aug. 3, 2016

(86) PCT No.: PCT/IB2016/054685
§ 371 (c)(1),
(2) Date: Feb. 1, 2018

(87) PCT Pub. No.: WO2017/021908
PCT Pub. Date: Feb. 9, 2017

(65) Prior Publication Data
US 2018/0224431 A1 Aug. 9, 2018

Related U.S. Application Data

(60) Provisional application No. 62/200,310, filed on Aug. 3, 2015.

(51) Int. Cl.
| | | |
|---|---|---|
| *A61K 31/496* | (2006.01) | |
| *A61P 35/00* | (2006.01) | |
| *G01N 33/50* | (2006.01) | |
| *A61K 31/47* | (2006.01) | |
| *A61K 31/4439* | (2006.01) | |
| *A61K 31/501* | (2006.01) | |

(52) U.S. Cl.
CPC ..... *G01N 33/5014* (2013.01); *A61K 31/4439* (2013.01); *A61K 31/47* (2013.01); *A61K 31/496* (2013.01); *A61K 31/501* (2013.01); *A61P 35/00* (2018.01); *G01N 33/5088* (2013.01); *C12Q 2600/142* (2013.01); *G01N 2333/46* (2013.01); *G01N 2333/495* (2013.01); *G01N 2800/222* (2013.01); *G01N 2800/50* (2013.01)

(58) Field of Classification Search
None
See application file for complete search history.

(56) References Cited

U.S. PATENT DOCUMENTS

2016/0333419 A1* 11/2016 Tse ............... C12Q 1/6886

FOREIGN PATENT DOCUMENTS

| JP | 2017-508443 A | 3/2016 |
|---|---|---|
| WO | 2011076786 | 6/2011 |
| WO | 2013/111105 | 8/2013 |
| WO | 2014/020502 A2 | 2/2014 |
| WO | 2015084804 | 6/2015 |
| WO | 2015/108175 A1 | 7/2015 |
| WO | 2016153006 | 9/2016 |

OTHER PUBLICATIONS

Iancu-Rubin et al., "Activation of p53 by the MDM2 inhibitor RG7112 impairs thrombopoiesis", Experimental Hematology, 2014, vol. 42, pp. 137-145.
Leon Centre et al., "Effect of the MDM2 antagonist RG7112 on the P53 pathway in patients with MDM2-amplified, well-differentiated or dedifferentiated liposarcoma: an exploratory proof-of-mechanism study", Lancet Oncology, 2012, vol. 13, pp. 1133-1140.
Na et al., "Expression of serum GDFI5 and its clinical significance in multiple myeloma patients", Journal of Central South University, Medical Science, 2014, vol. 39, No. 3, pp. 270-275.
Chawla et al., "Phase Ib study of RG7112 with doxorubicin (D) in advanced soft tissue sarcoma (ASTS)", Journal of Clinical Oncology, 2013, vol. 31, abstract 10514.
Vasiliou et al., "47th annual meeting of the American Society of Clinical Oncology (ASCO) 2011 focus on first-in-human and phase I trials", Drugs of the Future, 2011, vol. 36, No. 10, pp. 783-792.
Yee et al., "Phase 1b study of the MDM2 antagonist RG7112 in combination with 2 doses/schedules of cytarabine", Blood, 2013, vol. 122, No. 21, abstract 498.
Schwartz, "Development of MDM2 inhibitors for cancer therapy", 12th International Congress on Targeted Anticancer Therapies, 2014, pp. 1-26.
Wade, et al "MDM2, MDMX and p53 in Oncogenesis and Cancer Therapy" Nature Reviews, vol. 13, Feb. 2013, pp. 83-96.
Patnaik, "Clinical pharmacology characterization of RG7112, an MDM2 antagonist, in patients with advanced solid tumors" Cancer Chemother Pharmacol, Jul. 26, 2015, vol. 76, p. 587-595.
Zhao, "Small-Molecule Inhibitors of the MDM2-p53 Protein-Protein Interaction (MDM2 Inhibitors) in Clinical Trials for Cancer Treatment: Miniperspective", Journal of Medicinal Chemistry, Feb. 12, 2015, vol. 58 No. 3, p. 1038-10525.
Jeay, "Dose and schedule determine distinct molecular mechanisms underlying the efficacy of the p53-MDM2 inhibitor HDM201", Cancer Research, 2018, vol. 78 No. 21, p. 6257-6267.
Kumamoto, "Nutlin-3a activates p53 to both down-regulate inhibitor of growth 2 and up-regulate mir-34a, mir-34b, and mir-34c expression, and induce Senescence", Cancer Research, 2008, vol. 68 No. 9, p. 3193-3203.

* cited by examiner

*Primary Examiner* — Channing S Mahatan
(74) *Attorney, Agent, or Firm* — David K. Cheung

(57) ABSTRACT

The present disclosure relates to use of GDF-15 as a safety biomarker for determining a toxicological effect of a Mdm2 inhibitor; an ex vivo method for determining a toxicological effect of a Mdm2 inhibitor in a subject, in particular for determining a likelihood of developing thrombocytopenia in a subject in response to administration of a dose of a Mdm2 inhibitor; methods of using a Mdm2 inhibitor in the treatment of cancer in a subject; a kit for use in predicting the likelihood that a patient having cancer will develop thrombocytopenia in response to a treatment with a dose of a Mdm2 inhibitor; a kit for use in treating a patient having cancer and related disclosure embodiments.

14 Claims, 8 Drawing Sheets

GDF-15 AS A HAEMATOLOGICAL TOXICITY BIOMARKER

FIELD OF THE DISCLOSURE

The present disclosure relates to use of a safety biomarker for determining a toxicological effect of a Mdm2 inhibitor; an ex vivo method for determining a toxicological effect of a Mdm2 inhibitor in a subject, in particular for determining a likelihood of developing thrombocytopenia in a subject in response to administration of a dose of a Mdm2 inhibitor; methods of using a Mdm2 inhibitor in the treatment of cancer in a subject; a kit for use in predicting the likelihood that a patient having cancer will develop thrombocytopenia in response to treatment with a dose of a Mdm2 inhibitor; a kit for use in treating a patient having cancer and related disclosure embodiments.

BACKGROUND OF THE DISCLOSURE

The protein p53 is a transcription factor that controls the expression of a multitude of target genes involved in DNA damage repair, apoptosis and cell cycle arrest. Mutations, which lead to loss of wild-type p53 activity frequently detected in many different tumor types. The TP53 gene is one of the most frequently mutated genes in human cancers. Thus, tumor suppressor p53 is functionally impaired by mutation or deletion in nearly 50% of human cancers. In the remaining human cancers, p53 retains wild-type status but its function is inhibited by its primary cellular inhibitor, the murine double minute 2 (Mdm2, MDM2; HDM2 (human homolog of murine double minute 2)). Mdm2 is a negative regulator of the p53 tumor suppressor. Mdm2 protein functions both as an E3 ubiquitin ligase, that leads to proteasomal degradation of p53, and an inhibitor of p53 transcriptional activation. Often Mdm2 is found amplified in p53 wild-type tumors.

Because the interaction between Mdm2 and p53 is a primary mechanism for inhibition of the p53 function in cancers, which are retaining wild-type p53, targeting the Mdm2-p53 interaction, and thus reactivating p53, is a new promising therapeutic strategy. Several Mdm2 inhibitors have been developed that inhibit Mdm2-p53 interaction, and thus can elicit antineoplastic effect. The very first potent small-molecule Mdm2 inhibitors reported were Nutlins (Vassilev L T, et al., Science. 2004 Feb. 6; 303(5659):844-8). The discovery of Nutlins was followed by development of several further small-molecule Mdm2 inhibitors, such as MI-63 (Ding K, et al., J Med Chem. 2006 Jun. 15; 49(12): 3432-5), and MI219 (Shangary S, et al., Proc Natl Acad Sci USA. 2008 Mar. 11; 105(10):3933-8).

When drugs are translated to the clinic, attention needs to be paid to a certain toxicological effects of those drugs. Certain drugs may cause development of drug-induced thrombocytopenia, a condition in which a subject has a relative decrease of thrombocytes. Results, obtained from a proof of concept study in patients with liposarcomas of single-agent RG-7112, an inhibitor in the Nutlin family, demonstrated that RG-7112 induced thrombocytopenia in 40% of patients. This finding indicates that one of the major dose-limiting toxicities associated with RG7112 administration is thrombocytopenia (Ray-Coquard I, et al. Lancet Oncol, 2012, 13: 1133-1140). Studies carried out on an animal model indicate that RG7112-induced thrombocytopenia occurred rather late during the treatment period and persisted after drug discontinuation, suggesting that the drug acts on early hematopoietic progenitor cells (Iancu-Rubin, C., et al., Experimental Hematology 2014; 42:137-145). Other Mdm2 inhibitors, not only RG-7112, may potentially induce thrombocytopenia, and thus care should be taken in this respect.

It is important to adjust treatment of susceptible patients before development of thrombocytopenia or at the very early onset of thrombocytopenia either by discontinuing the treatment with that particular drug that can cause thrombocytopenia or by altering the treatment correspondingly. Failure to detect an onset of thrombocytopenia at an early stage and continuation of the treatment with the drug in question may lead to a fatal outcome. Thus, there is a continuing need in the art for predicting, determining, monitoring delayed drug-induced thrombocytopenia, and managing toxicity in a subject after drug treatment, in particular after administration of a Mdm2 inhibitor.

SUMMARY OF THE DISCLOSURE

It is an object of the present disclosure to provide GDF-15 as a safety biomarker for determining a toxicological effect of a Mdm2 inhibitor, in particular hematotoxicity of a Mdm2 inhibitor. In particular, the present disclosure relates to use of GDF-15 as a safety biomarker for determining the likelihood of developing thrombocytopenia in a subject in response to administrationof a Mdm2 inhibitor.

In accordance with the present disclosure it has been surprisingly found that there is a correlation between (i) a relative increase of the level of GDF-15 expression in a subject after administration of a dose of a Mdm2 inhibitor in comparison to a baseline level of expression of GDF-15 in the same subject, and (ii) a toxicological effect of administration of said dose of said Mdm2 inhibitor, in particular hematotoxicity of a Mdm2 inhibitor. It has been identified that, for a given dosing regimen, there is a correlation between the level of GDF-15 expression after administration of a dose of a Mdm2 inhibitor to a subject and the likelihood of developing thrombocytopenia in the subject in response to said dose of the Mdm2 inhibitor. In particular, it was established that at least 25% increase, particularly at least 50% increase of GDF-15 expression in a post-administration sample obtained from a subject after a dose of a Mdm2 inhibitor administration in comparison to a pre-administration sample obtained from the subject before Mdm2 inhibitor administration is indicative of an increased likelihood that the patient will develop thrombocytopenia in response to said dose of the Mdm2 inhibitor. The use of GDF-15 as a safety biomarker can help a physician to monitor the course of treatment of a subject (patient) with a Mdm2 inhibitor and predict delayed drug-induced thrombocytopenia early enough to properly apply measures to minimize thrombocytopenia or prevent it altogether.

In one aspect, the present disclosure relates to an ex vivo method for determining a toxicological effect of a Mdm2 inhibitor in a subject, the method comprising the steps of:
(i) providing a pre-administration biological sample obtained from a subject prior to administration of said Mdm2 inhibitor;
(ii) measuring expression of GDF-15 in the pre-administration sample;
(iii) administering a dose of said Mdm2 inhibitor to the subject;
(iv) providing a post-administration biological sample obtained from the subject after the administration of said Mdm2 inhibitor;
(v) measuring expression of GDF-15 in the post-administration samples;

(vi) comparing expression of GDF-15 in the pre-administration sample with the level of expression of GDF-15 in the post-administration sample, in particular wherein the likelihood of developing thrombocytopenia in a subject in response to administration of said dose of the Mdm2 inhibitor is determined.

In another aspect, the disclosure provides a Mdm2 inhibitor for use in the treatment of cancer in a subject, comprising
(i) measuring GDF-15 expression in a pre-administration biological sample obtained from said subject before a dose of the Mdm2 inhibitor has been administered to said subject;
(ii) measuring GDF-15 expression in a post-administration biological sample obtained from said subject after a dose of the Mdm2 inhibitor has been administered to said subject;
(iii) comparing the GDF-15 expression in the pre-administration sample with the GDF-15 expression in the post-administration sample; and
(iv) altering the treatment of said subject, when the GDF-15 expression in the post-administration sample is at least 25%, preferably at least 50% higher in comparison with the GDF-15 expression in the pre-administration sample; or
(v) making no changes to the administration regimen of said Mdm2 inhibitor to said subject, when the level of GDF-15 expression in the post-administration sample is less than 50%, preferably less than 25% higher in comparison with the GDF-15 expression in the pre-administration sample.

In a further aspect, the present disclosure relates to a kit for use in predicting the likelihood that a patient having cancer will develop thrombocytopenia in response to a treatment with a dose of a Mdm2 inhibitor comprising
(i) at least one probe capable of detecting the GDF-15 expression; and
(ii) instructions for using the probe to assay a biological sample obtained from the patient for the GDF-15 expression, wherein
  (a) at least 25% increase, more preferably at least 50% increase of GDF-15 expression after administration of said dose of said Mdm2 inhibitor to said patient is indicative of an increased likelihood that said patient will develop thrombocytopenia in response to the treatment with said dose of the Mdm2 inhibitor, and
  (b) less than 50% increase, more preferably less than 25% increase in GDF-15 expression after administration of said dose of said Mdm2 inhibitor to said patient is indicative of a decreased likelihood that said patient will develop thrombocytopenia in response to the treatment with said dose of the Mdm2 inhibitor.

In yet a further aspect, the present disclosure relates to a kit for use in treating a patient having cancer comprising:
(i) a therapeutically effective amount of a Mdm2 inhibitor;
(ii) at least one probe capable of detecting the GDF-15 expression;
(iii) instructions for using the probe to assay a biological sample obtained from the patient for the GDF-15 expression; and
(iv) instructions for applying the means to the patient if the biological sample obtained from the patient after the therapeutically effective amount of the Mdm2 inhibitor has been administered to the patient has at least 25% increased, more preferably at least 50% increased GDF-15 expression in comparison to the level of GDF-15 expression in a pre-administration sample obtained from said patient.

Specifically, the present disclosure provides the following aspects, advantageous features and specific embodiments, respectively alone or in combination, as listed in the following items:

1. Use of GDF-15 as a safety biomarker for determining a toxicological effect of a Mdm2 inhibitor.
2. An ex vivo method for determining a toxicological effect of a Mdm2 inhibitor in a subject, the method comprising the steps of:
   (i) providing a pre-administration biological sample obtained from said subject prior to administration of said Mdm2 inhibitor;
   (ii) measuring expression of GDF-15 in the pre-administration sample;
   (iii) administering a dose of said Mdm2 inhibitor to the subject;
   (iv) providing a post-administration biological sample obtained from the subject after the administration of said Mdm2 inhibitor;
   (v) measuring expression of GDF-15 in the post-administration samples;
   (vi) comparing expression of GDF-15 in the pre-administration sample with the level of expression of GDF-15 in the post-administration sample.
3. The method according to item 2, wherein the likelihood of developing thrombocytopenia in said subject in response to administration of said dose of the Mdm2 inhibitor is determined.
4. The method of item 2 or item 3, wherein less than 50% increase, more preferably less than 25% increase of GDF-15 expression in said post-administration sample in comparison to said pre-administration sample is indicative of a decreased likelihood that the patient will develop thrombocytopenia in response to administration of said dose of the Mdm2 inhibitor.
5. The method of any one of items 2 to 4, wherein at least 25% increase, more preferably 50% increase of GDF-15 expression in said post-administration sample in comparison to said pre-administration sample is indicative of an increased likelihood that the patient will develop thrombocytopenia in response to the administration of said dose of the Mdm2 inhibitor.
6. Mdm2 inhibitor for use in the treatment of cancer in a subject, comprising
   (i) measuring GDF-15 expression in a pre-administration biological sample obtained from said subject before a dose of the Mdm2 inhibitor has been administered to said subject;
   (ii) measuring GDF-15 expression in a post-administration biological sample obtained from said subject after a dose of the Mdm2 inhibitor has been administered to said subject;
   (iii) comparing the GDF-15 expression in the pre-administration sample with the GDF-15 expression in the post-administration sample; and
   (iv) altering the treatment of said subject, when the GDF-15 expression in the post-administration sample is at least 25% higher, preferably at least 50% higher in comparison with the GDF-15 expression in the pre-administration sample; or
   (v) making no changes to the administration regimen of said Mdm2 inhibitor to said subject, when the level of GDF-15 expression in the post-administration sample is less than 50%, preferably less than 25% higher in comparison with the GDF-15 expression in the pre-administration sample.
7. The Mdm2 inhibitor according to item 6, wherein said alteration of the treatment comprises alteration of the administration regimen of said Mdm2 inhibitor to the subject and/or administering the means for reducing the Mdm2 inhibitor effect on thrombocytes.
8. The Mdm2 inhibitor according to item 6 or item 7, wherein said alteration of the treatment comprises a reduction of a dose of said Mdm2 inhibitor, and/or reduction of a frequency of administration of said Mdm2 inhibitor.
9. The Mdm2 inhibitor according to item 6 or item 8, wherein the means for reducing the Mdm2 inhibitor effect on thrombocytes comprise platelet transfusion and/or administration of thrombopoietin, and/or administration of thrombopoietin receptor agonist, preferably comprise platelet transfusion.
10. The Mdm2 inhibitor according to any one of items 6 to 9, wherein the means for reducing the Mdm2 inhibitor effect on thrombocytes comprise administration of a thrombopoietin receptor agonist, and wherein said thrombopoietin receptor agonist is eltrombopag.
11. The Mdm2 inhibitor for use in the treatment of cancer according to any one of items 6 to 10, wherein said alteration of the treatment comprises a discontinuation of the treatment with said Mdm2 inhibitor.
12. The Mdm2 inhibitor for use in the treatment of cancer according to any one of items 6 to 10, wherein said treatment alteration comprises a drug holiday.
13. The method of any one of items 2 to 5 or the Mdm2 inhibitor of any one of items 6 to 12, wherein said post-administration sample is obtained within a timeframe of from about 30 min to about 24 hours, preferably from about 1 hour to about 12 hours, from about 2 hours to about 12 hours, about 3 hours to about 12 hours, from about 4 hours to about 8 hours, from about 5 hours to about 8 hours, about 5 hours to about 7 hours, about 6 hours to about 7 hours after administration of the Mdm2 inhibitor.
14. The method of item 13 or the Mdm2 inhibitor of item 13, wherein said post-administration sample is obtained about 30 min, about 1 hour, about 2 hours, about 3 hours, about 4 hours, about 5 hours, about 6 hours, about 7 hours, about 8 hours, about 10 hours, about 12 hours, about 24 hours after administration of the Mdm2 inhibitor.
15. The method of item 14 or the Mdm2 inhibitor of item 13, wherein said post-administration sample is obtained about 3 hours after administration of the Mdm2 inhibitor.
16. The method of item 14 or the Mdm2 inhibitor of item 13, wherein said post-administration sample is obtained about 6 hours after administration of the Mdm2 inhibitor.
17. The method of item 14 or the Mdm2 inhibitor of item 13, wherein said post-administration sample is obtained about 12 hours after administration of the Mdm2 inhibitor.
18. The method according to any one of items 2 to 5, 13 to 17 or the Mdm2 inhibitor according to any one of items 6 to 17, wherein said GDF-15 expression is assayed by measuring GDF-15 gene transcription.
19. The method according to item 18 or the Mdm2 inhibitor according to item 18, wherein said GDF-15 gene expression is assayed by means of an oligonucleotide probe that specifically hybridizes to a region of a nucleic acid coding for GDF-15.
20. The method of any one of items 2 to 5, 13 to 17 or the Mdm2 inhibitor of any one of items 6 to 17, wherein said GDF-15 expression is assayed by measurement of GDF-15 protein level in a biological sample.
21. The method according to item 20 or the Mdm2 inhibitor according to item 20, wherein said GDF-15 protein level is assayed by means of an antibody that binds to GDF-15 protein.
22. The method of any one of items 20 to 21 or the Mdm2 inhibitor of any one of items 20 to 21, wherein the biological sample is blood, plasma, serum or urine.
23. The method of any one of items 20 to 21 or the Mdm2 inhibitor of any one of items 20 to 21, wherein the biological sample is blood.
24. The method of any one of items 2 to 5, 13 to 23 or the Mdm2 inhibitor of any one of items 6 to 23, wherein GDF-15 expression in the post-administration sample of at least 75%, 100% or 150% increase in comparison with the GDF-15 expression in the pre-administration sample is indicative of the increased likelihood for developing thrombocytopenia.
25. A kit for use in predicting the likelihood that a patient having cancer will develop thrombocytopenia in response to the treatment with a dose of a Mdm2 inhibitor comprising
    (i) at least one probe capable of detecting the GDF-15 expression; and
    (ii) instructions for using the probe to assay a biological sample obtained from the patient for the GDF-15 expression, wherein
        (a) at least 25% increase, more preferably at least 50% increase of GDF-15 expression after administration of said dose of said Mdm2 inhibitor to said patient is indicative of an increased likelihood that said patient will develop thrombocytopenia in response to the treatment with said dose of the Mdm2 inhibitor, and
        (b) less than 50% increase, more preferable less than 25% increase in GDF-15 expression after administration of said dose of said Mdm2 inhibitor to said patient is indicative of a decreased likelihood that said patient will develop thrombocytopenia in response to said the treatment with said dose of the Mdm2 inhibitor.
26. A kit for use in treating a patient having cancer comprising:
    (i) a therapeutically effective amount of a Mdm2 inhibitor;
    (ii) at least one probe capable of detecting the GDF-15 expression;
    (iii) instructions for using the probe to assay a biological sample obtained from the patient for the GDF-15 expression; and
    (iv) instructions for applying the means to the patient if the biological sample obtained from the patient after the therapeutically effective amount of the Mdm2 inhibitor has been administered to the patient has at least 25% increased, more preferably at least 50% increased GDF-15 expression in comparison to the level of GDF-15 expression in a pre-administration sample obtained from said patient.
27. The kit according to any one of items 25 to 26, wherein the probe is an oligonucleotide that specifically hybridizes to a region of a nucleic acid coding for GDF-15, or an antibody that binds to GDF-15 protein.
28. The use according to item 1, or the method according to any one of items 2 to 5, or 12 to 24, or the Mdm2 inhibitor according to any one of items 6 to 24, or the kit according to any one of items 25 to 27, wherein said Mdm2 inhibitor is selected from the group consisting of:

(S)-1-(4-Chloro-phenyl)-7-isopropoxy-6-methoxy-2-(4-{methyl-[4-(3-oxo-piperazin-1-yl)-trans-cyclohexylmethyl]-amino}-phenyl)-1,4-dihydro-2H-isoquinolin-3-one;

(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one;

(S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one;

(S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one;

(S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one;

1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one;

(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;

(S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

(S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;

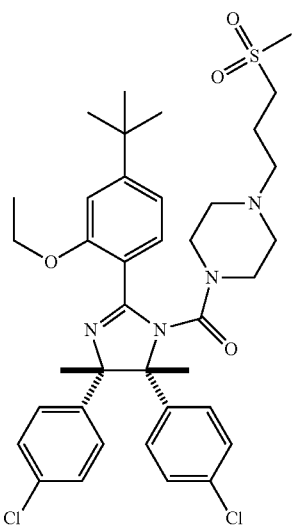

RG7112

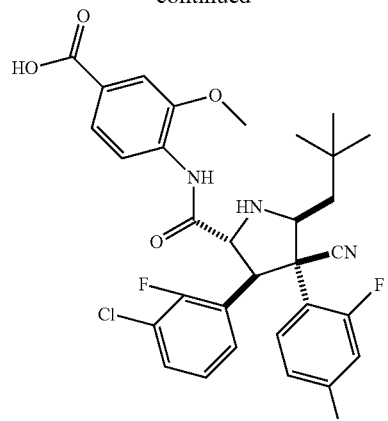

RG7388

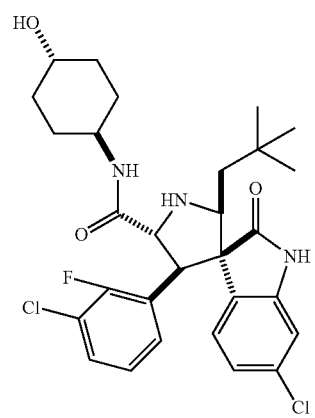

SAR299155

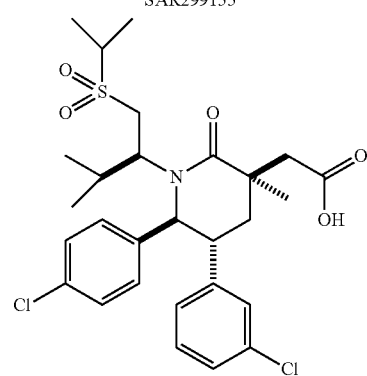

AMG 232

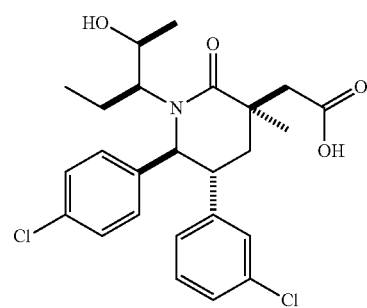

AM-8553

-continued

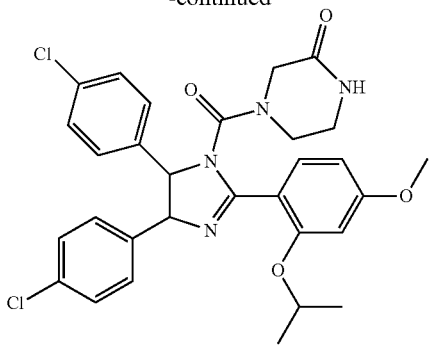

Nutlin-3

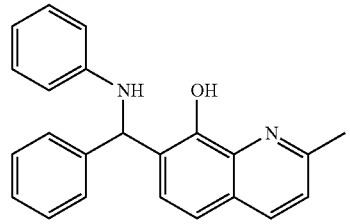

NSC 66811

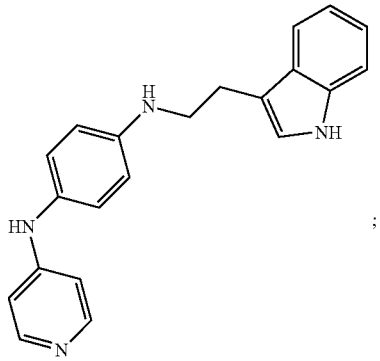

JNJ-26854165 and
(S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one; or a pharmaceutically acceptable salt of any of the foregoing.

29. The use according to item 1, or the method according to any one of items 2 to 5, or 12 to 24, or the Mdm2 inhibitor according to any one of items 6 to 24, or the kit according to any one of items 25 to 27, wherein said Mdm2 inhibitor is (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof.

30. The use according to item 1, or the method according to any one of items 2 to 5, or 12 to 24, or the Mdm2 inhibitor according to any one of items 6 to 24, or the kit according to any one of items 25 to 27, wherein said Mdm2 inhibitor is (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, or a pharmaceutically acceptable salt thereof.

31. Thrombopoietin receptor agonist for use in the prevention or treatment of drug-induced thrombocytopenia in a subject for which the GDF-15 expression in a post-administration sample is at least 25%, preferably at least 50%, higher in comparison with a GDF-15 expression in the pre-administration sample;

wherein the "GDF-15 expression in a pre-administration sample" is the GDF-15 expression measured in a pre-administration biological sample obtained from said subject before a dose of a drug, which may cause development of drug-induced thrombocytopenia, has been administered to said subject;

and wherein the "GDF-15 expression in a post-administration sample" is the GDF-15 expression measured in a post-administration biological sample obtained from said subject after a dose of the drug, which may cause development of drug-induced thrombocytopenia, has been administered to said subject.

32. Thrombopoietin receptor agonist for use according to items 31 or 32 wherein the drug which may cause development of drug-induced thrombocytopenia is a Mdm2 inhibitor.

33. A combination of a Mdm2 inhibitor and a thrombopoietin receptor agonist.

34. A combination according to items 33 for medical use.

35. The combination according to items 33 for use in the treatment of cancer and the prevention or treatment of drug-induced thrombocytopenia.

36. Thrombopoietin receptor agonist, the combination, or the combination for use according to any one of items 31 to 35, wherein the thrombopoietin receptor agonist is eltrombopag.

37. Thrombopoietin receptor agonist, the combination, or the combination for use according to any one of items 31 to 36 wherein the Mdm2 inhibitor is (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof.

38. Thrombopoietin receptor agonist, the combination, or the combination for use according to any one of items 31 to 36 wherein the Mdm2 inhibitor is (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, or a pharmaceutically acceptable salt thereof.

(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one. Each point represents an individual patient; X coordinate represents GDF-15 increase in percentage change (%) from baseline; Y coordinate being the lowest observed platelet count for the same patient during the course of the treatment.

Figure 4:
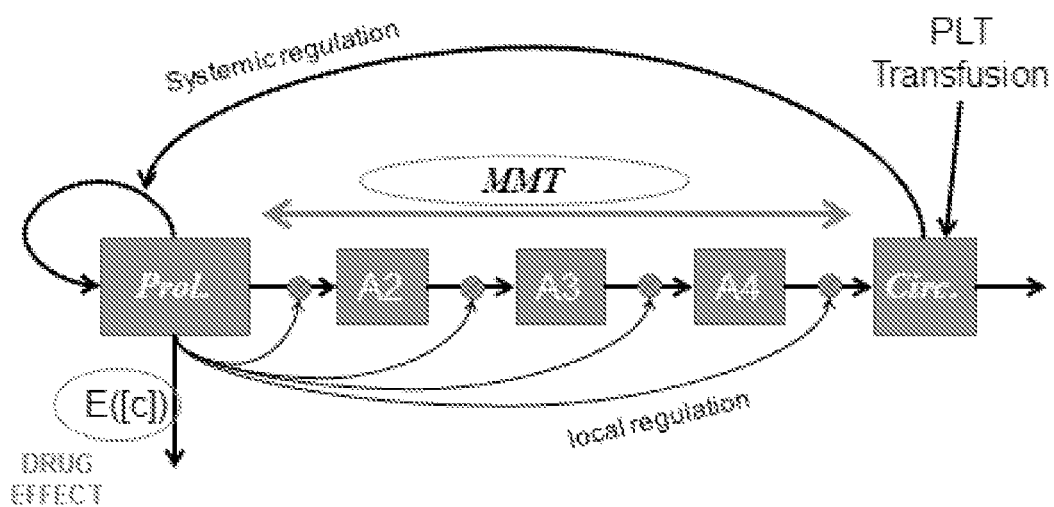

FIG. 4 PKPD model used to describe platelets kinetics. MMT is the mean maturation time, E([C]) is a drug effect function of drug concentration. Circ. compartment represents circulating platelets, Prol.—proliferative immature cells and A2, A3, A4—maturation compartments.

Figure 5:
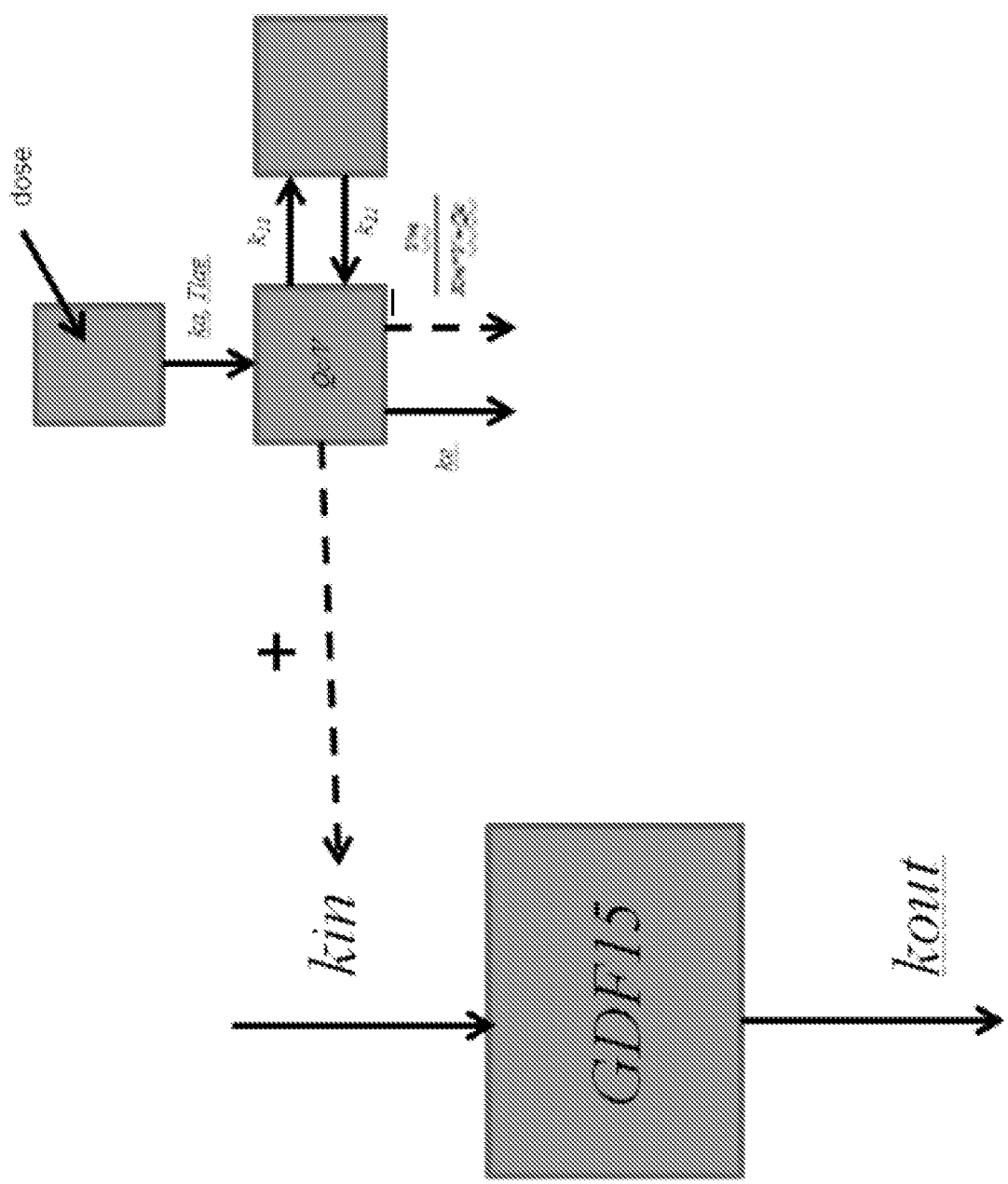

FIG. 5 Schematic representation of the PKPD model used to describe GDF-15 kinetics. Tlag and ka are delay and first order drug absorption rate parameters respectively. k12 and k21 intercompartmental rates, ke elimination rate, Vm and km Michaelis Menten elimination parameters. kout is the turnover rate of the indirect response model and kin the zero order production. V is the apparent volume of the central compartment and Qc/V the drug concentration.

Figure 6:
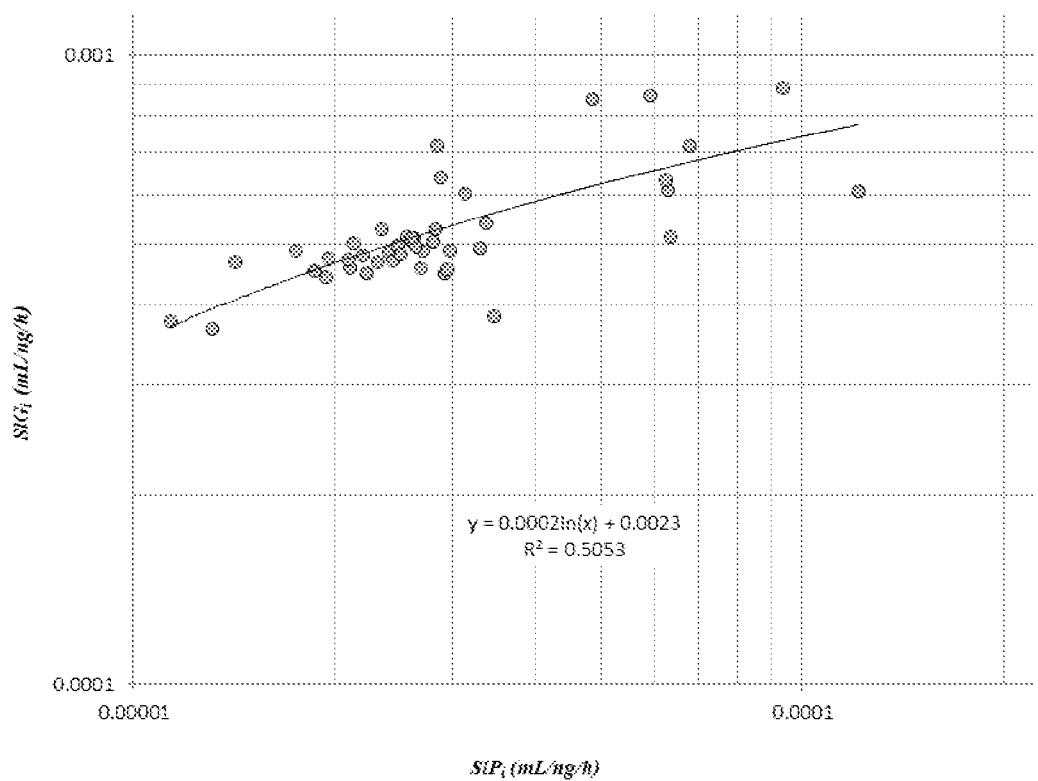

FIG. 6 Established PKPD model. Individual drug potency on GDF-15 slGi production was plotted against the individual drug potency on immature hematopoietic cells slPi.

Figure 7:
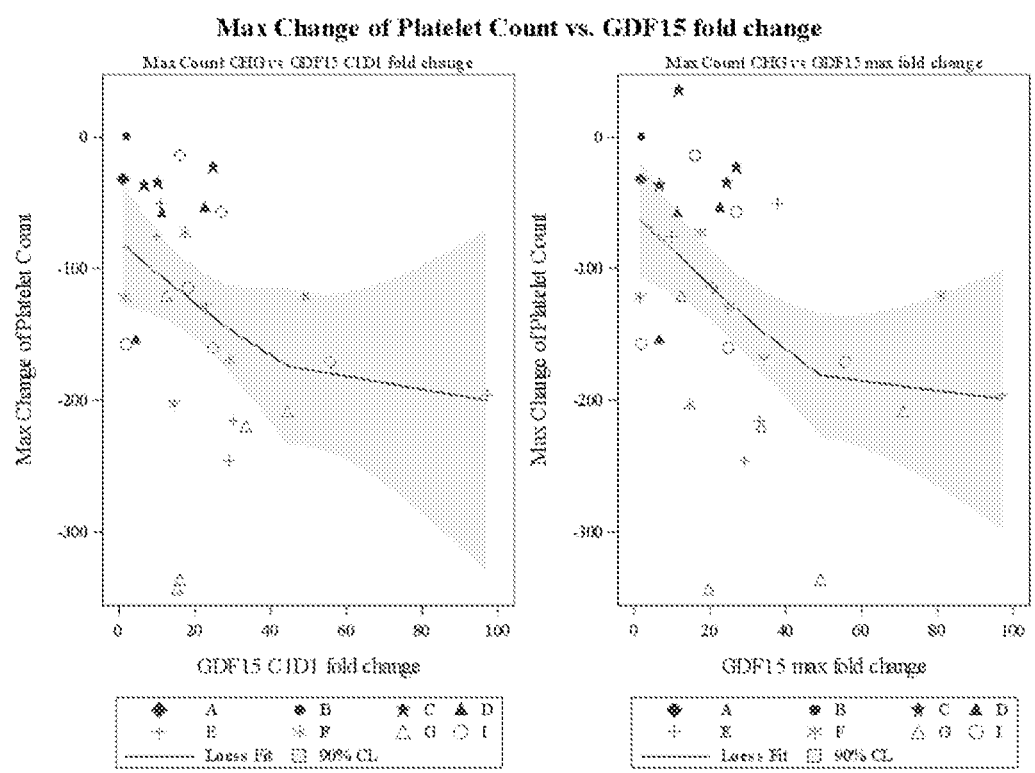
Figure 8:
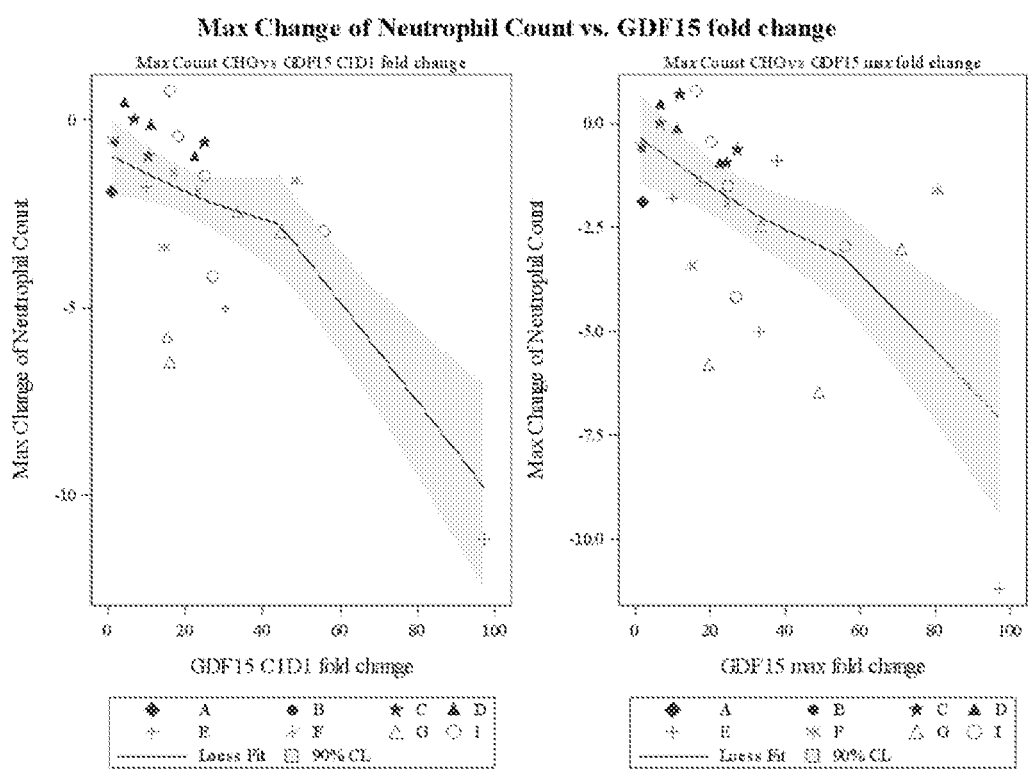

FIG. 7 and FIG. 8 Maximum change of platelet count (FIG. 7) and neutrophil count (FIG. 8) vs. GDF-15 fold change for patients with solid tumors receiving compound of formula I on the first day of a three week cycle (herein also referred to as regimen 1A or q3w) in doses of 12.5 mg (A), 25 mg (B), 50 mg (C), 100 mg (D), 200 mg (E), 250 mg (F), 350 mg(G) or on the first and eighth day of a 4 week cycle (herein also referred to as regimen 1B) in a dose of 120 mg (I). Left graphs: Maximum platelet count change vs. GDF-15 fold change, the GDF-15 being measured on day 1 of the first cycle (C1D1). Right graphs: Maximum platelet count change vs. GDF-15 fold change.

DETAILED DESCRIPTION OF THE DISCLOSURE

Administration of a Mdm2 inhibitor to a patient may cause development of thrombocytopenia. Previous studies demonstrated that Mdm2 inhibitor RG7112 impairs thrombopoesis. The inventors have identified GDF-15 as a safety biomarker for determining toxicological effect of a Mdm2 inhibitor. The disclosure is based on the identification of a correlation between (i) a relative increase, in comparison to a baseline level of expression of GDF-15 in a subject, of the level of GDF-15 expression in the same subject after administration of a Mdm2 inhibitor, and (ii) a toxicological effect of said Mdm2 inhibitor, in particular hematotoxicity of a Mdm2 inhibitor. The slope of the link may vary depending on the potency of the Mdm2 and the dosing regimen. In particular, the inventors have identified that, for a given dosing regimen, there is a correlation between the level of GDF-15 expression after administration of a dose of a Mdm2 inhibitor and the likelihood of developing thrombocytopenia in a subject in response to administration of said dose of the Mdm2 inhibitor. Advantageously, the disclosure can be used to determine the likelihood of developing thrombocytopenia in a subject for a given dosing regimen of a Mdm2 inhibitor at the very early onset of thrombocytopenia or even before thrombocytopenia develops. In particular, the disclosure can be used to determine the likelihood of developing thrombocytopenia in a subject for a given dosing regimen of a Mdm2 inhibitor already after the $1^{st}$ day of the $1^{st}$ cycle of administration of a therapeutically effective amount of a Mdm2 inhibitor. In another example, the disclosure can be used to determine the likelihood of developing thrombocytopenia in a subject for a given dosing regimen of a Mdm2 inhibitor after from the $1^{st}$ day of the $1^{st}$ cycle up to the $7^{th}$ day of the $1^{st}$ cycle of administration of a therapeutically effective amount of a Mdm2 inhibitor, in particular after the $1^{st}$ day of the $1^{st}$ cycle, after the $2^{nd}$ day of the $1^{st}$ cycle, or after the $3^{rd}$ day the $1^{st}$ cycle of administration of a therapeutically effective amount of a Mdm2 inhibitor. By applying the teaching of the present disclosure a skilled person can arrive at the correlation parameters linking the relative increase in GDF-15 expression in a pre- and post-administration samples obtained from a subject to the likelihood of developing thrombocytopenia in response to the treatment of a given Mdm2 inhibitor in the same subject.

In one aspect, the present disclosure relates to use of GDF-15 as a safety biomarker for determining a toxicological effect of a Mdm2 inhibitor, in particular hematotoxicity of a Mdm2 inhibitor. In one embodiment, the present disclosure relates to use of GDF-15 as a safety biomarker for determining the likelihood of developing thrombocytopenia in a subject in response to administration of a dose of Mdm2 inhibitor.

A "subject," "individual" or "patient" is used interchangeably herein, which refers to a vertebrate, preferably a mammal, more preferably a human. Mammals include, but are not limited to, mice, simians, humans, farm animals, sport animals, and pets.

The term "toxicological effect", as used herein, refers to the effect on a whole organism as well as the effect on a substructure of the organism. Specifically, the term refers to the effect that leads to thrombocytopenia in the organism. The term "hematotoxicity", as used herein, refers to toxicity to the hematopoietic system resulting into damage of the blood producing tissues, causing a decrease of the white blood cell count and/or absolute neutrophil count.

The term "thrombocytopenia", as used herein, refers to a reduced number of platelets, which is below the normal blood platelet count (i.e. below 150,000 platelets per microliter). It can be caused by dysregulation of megakaryocytopoiesis, which leads to the reduction of a number of platelets. Megakaryocytopoiesis is a process of proliferation of bone marrow hematopoietic progenitor cells, maturation, platelet formation, and the release of platelets into circulation. A normal platelet count in adults ranges from 150,000 to 450,000 platelets per microliter of blood (Ross D W; Ayscue L H; Watson J; Bentley S A (1988). "Stability of hematologic parameters in healthy subjects. Intraindividual versus interindividual variation". American journal of clinical pathology 90 (3): 262-7). A platelet count of less than 150,000 platelets per microliter is lower than normal, and indicative of thrombocytopenia. At platelet counts<10,000/μL, spontaneous bleeding is increased. At platelet counts<50,000/μL, surgical procedures are often complicated by bleeding. At platelet counts<100,000/μL, chemotherapy and radiation therapy are administered with caution for fear of worsening the thrombocytopenia and increasing the risk of bleeding. According to the NCI Common Terminology Criteria for Adverse Events v3.0, thrombocytopenia is classified as following: grade 1 (mild adverse event) is characterized by a platelet counts<LLN (Lower Limit of Normal)—75,000/mm³, grade 2 (moderate adverse event) is characterized by a platelet counts<75,000/mm³-50,000/mm³, grade 3 (severe adverse event) is at platelet counts<50,000/mm³-25,000/mm³, grade 4 (life-threatening or disabling adverse event) is at platelet counts<25,000/mm³ (Common Terminology Criteria for Adverse Events v3.0 (CTCAE), Aug. 9, 2006; http://ctep.cancer.gov/protocolDevelopment/electronic_applications/docs/ctcaev3.pdf).

As used herein, "likelihood" and "likely" is a measurement of how probable an event is to occur. It may be used interchangeably with "probability". Likelihood refers to a probability that is more than speculation, but less than certainty. Thus, an event is likely if a reasonable person using common sense, training or experience concludes that, given the circumstances, an event is probable. In some embodiments, once likelihood has been ascertained, the patient may be treated (or treatment continued) with the compound or the treatment may need to be altered or discontinued. In one embodiment, the "likelihood" and "likely" denote a chance in percent of how probable an event is to occur.

The phrase "increased likelihood" refers to an increase in the probability that an event will occur. For example, some methods herein allow prediction of whether a patient will display an increased likelihood of developing thrombocytopenia in response to the administration of said Mdm2 inhibitor. In one embodiment the increased likelihood means that there is more than 50% chance, more than 60% chance, more than 70% or more than 80% chance that an event will occur. Equally, a "decreased likelihood" means, that the chance is lower than 50%, lower than 60%, lower than 70% or lower than 80%, respectively, that an event will occur.

The term "administration", "administering", or the like refers to a single administration of a therapeutic agent, as well as the term "administration" is also intended to include administration of a therapeutic agent according to a complete treatment regimens or dosing regimens. The term "administration" is also intended to include treatment regimens in which the therapeutic agents are not necessarily administered by the same route of administration or at the same time.

The term "continuous administration", as used herein, refers to a treatment regimen based on a given dosing of a therapeutic agent.

As used herein, the term "treatment regimen" or "a dosing regimen" refers to a dosing regimen wherein a therapeutic agent could be administered once every 1, 2, 3, 4, 5, 6, 7, 8, 9, 10, 11, 12, 13, 14, . . . 21, . . . , 26, 27, 28, 29, 30 . . . , 35, . . . , 42, . . . , 49, . . . , 56, 57, 58, 59, 60 days. This term comprises e.g. dosing regimens having (i) a dosing periodicity ranging from about once daily to about once every 60 days, (ii) a dosing periodicity ranging from about once every 2 days to about once every 40 days or 6 weeks, (iii) a dosing periodicity ranging from about once every 5 days to about once monthly or about once every 4 weeks or about once every 30 days, (iv) a dosing periodicity ranging from about once weekly or about once every 7 days to about once every 3 weeks or about once every 20 days, (v) a dosing periodicity ranging from about once weekly or about once every 7 days to about once biweekly or once every 10 days, or (vi) a dosing periodicity ranging from 2 times a week to 4 times a week, particularly 3 times a week. In every case the dosing can be followed by drug holiday. The dosing regimen once every 3 weeks is preferred.

The "treatment regimen" or "a dosing regimen" also include administering a therapeutic agent for a specific period of time followed by drug holiday. For example, the Mdm2 inhibitor can be administered 3 times a week continuously, or 3 times a week for 2 weeks followed by 1 week drug holiday (3 week cycle). In another example the inhibitor can be administered once daily, 2 weeks on, 2 weeks off. In yet another example the drug can be administered once daily for a period of 3 weeks with one week drug holiday (1 daily/3 weeks; drug holiday/1 week), followed by the next cycle(s) of drug administration (1 daily/3 weeks; drug holiday/1 week).

The term "GDF-15" (or "GDF15"), as used herein, refers to Growth differentiation factor 15, also known as MIC-1, TGF-PL, PDF, PLAB and PTGFB. The accession numbers for GDF-15 are Q99988, BC008962, GI:38196924, AAH08962. GDF-15 is a divergent member of transforming growth factor-beta super family. GDF-15 mRNA is most abundant in the liver, with lower levels seen in some other tissues.

As used herein, "GDF-15 expression", "level of GDF-15 expression" or the like refer to GDF-15 gene transcription or GDF-15 protein expression. GDF-15 gene expression can be assayed or measured, for example, by means of an oligonucleotide probe that specifically hybridizes to a region of a nucleic acid coding for GDF-15. GDF-15 protein level can be assayed or measured, for example, by means of an antibody that binds to GDF-15 protein, for example by ELISA assay. Often, GDF-15 gene or protein expression measurements are compared between each other, such as measurements pre- and post-treatment, and only a relative value or level of GDF-15 gene transcription or level of GDF-15 protein expression can be relevant.

The term "Mdm2 inhibitor" or "HDM2 inhibitor" as used herein, refer to any compound inhibiting the HDM2/p53 (Mdm2/p53) interaction association. HDM2 (Human homolog of murine double minute 2) is a negative regulator of p53. Mdm2inhibitors are useful in pharmaceutical compositions for human or veterinary use where inhibition of Mdm2/p53 association is indicated, e.g., in the treatment of tumors and/or cancerous cell growth. In particular, Mdm2 inhibitors are useful in the treatment of human cancer, since the progression of these cancers may be at least partially dependent upon overriding the "gatekeeper" function of p53, for example the overexpression of Mdm2.

Alternatively, instead of or in addition to a Mdm2 inhibitor, any other direct activator of the p53 pathway as part of their pharmacological mode of action may be used in the aspects of the present invention as described herein as p53 is used as a surrogate marker for p53 activation. E.g. as an alternative or in addition to a Mdm2 inhibitor a Mdm4 inhibitor may be used in the aspects of the present invention as described herein.

In a preferred embodiment, the "Mdm2 inhibitor" or "HDM2 inhibitor", as referred, inhibits the Mdm2/p53 interaction with an IC50 of less than 10 µM, preferably less than 1 µM, preferably in the range of nM, measured by a Time Resolved Fluorescence Energy Transfer (TR-FRET) Assay. Fluorescence energy transfer (or Foerster resonance energy transfer) describes an energy transfer between donor and acceptor 5 fluorescent molecules. For this assay, MDM2 protein (amino acids 2-188), tagged with a C-terminal Biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor 10 molecule at 340 nm, binding interaction between MDM2 and the p53 peptide induces energy transfer and enhanced response at the acceptor emission wavelength at 665 nm. Disruption of the formation of the p53-MDM2 complex due to an inhibitor molecule binding to the p53 binding site of MDM2 results in increased donor emission at 615 nm. The ratiometric FRET assay readout is calculated from the 15 raw data of the two distinct fluorescence signals measured in time resolved mode (countrate 665 nm/countrate 615 nm x 1000). The assay can be performed according to the following procedure: The test is performed in white 1536w microtiterplates (Greiner Bio-One GmbH, Frickenhausen, Germany) in a total volume of 3.1 μl by combining 100 nl of compounds diluted in 90% DMSO/10% H2O (3.2% final DMSO concentration) with 2 μl Europium 20 labeled streptavidin (final concentration 2.5 nM) in reaction buffer (PBS, 125 mM NaCl, 0.001% Novexin (consists of carbohydrate polymers (Novexin polymers), designed to increase the solubility and stability of proteins; Novexin Ltd., ambridgeshire, United Kingdom), Gelatin 0.01%, 0.2% Pluronic (block copolymer from ethylenoxide and propyleneoxide, BASF, Ludwigshafen, Germany), 1 mM DTT), followed by the addition of 0.5 μl MDM2-Bio or MDM4-Bio diluted in assay buffer (final concentration 10 nM). Allow the solution to pre-incubate for 15 minutes at room temperature, followed by addition of 0.5 μl Cy5-p53 peptide in assay buffer (final concentration 20 nM). Incubate at room temperature for 10 minutes prior to reading the plate. For measurement of samples, an Analyst GT multimode microplate reader (Molecular Devices) with the following settings 30 is used: Dichroic mirror 380 nm, Excitation 330 nm, Emission Donor 615 nm and Emission Acceptor 665 nm. IC50 values are calculated by curve fitting using XLfit. If not specified, reagents are purchased from Sigma Chemical Co, St. Louis, Mo., USA.

MDM2 (Mdm2) specifically relates to MDM2 as described in EMBO J. 10, 1565-9, Fakharzadeh et al., 1991. The accession numbers of MDM2 (Mdm2) are Q86WA3, AJ550519, GI:29125746. A variant of MDM2 (Mdm2) refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Reseach Park, Madison Wis., USA, which uses the algorithm of Smith and Waterman (Adv. Appl. Math. 2: 482-489 (1981), especially using an affine gap search with a gap open penalty of 12 and a gap extension penalty of 1.

"Variants thereof" where mentioned means one or more variant(s).

According to the present disclosure, a Mdm2 inhibitor can be for example a compound of any of the following formulas:
- (S)-1-(4-Chloro-phenyl)-7-isopropoxy-6-methoxy-2-(4-{methyl-[4-(3-oxo-piperazin-1-yl)-trans-cyclohexylmethyl]-amino}-phenyl)-1,4-dihydro-2H-isoquinolin-3-one;
- (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one;
- (S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one;
- (S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one;
- (S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one;
- 1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one;
- (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;
- 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;
- (S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;
- (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;

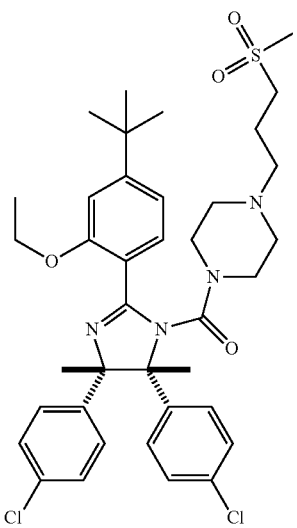

RG7112

-continued

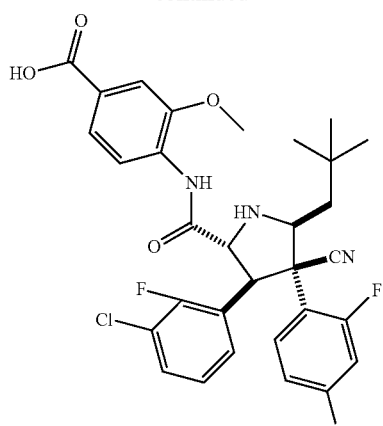

RG7388

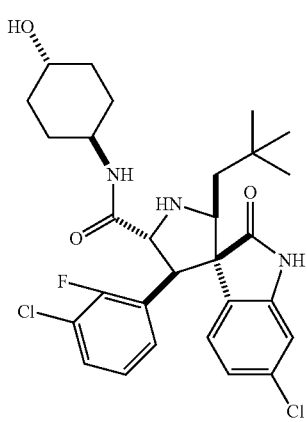

SAR299155

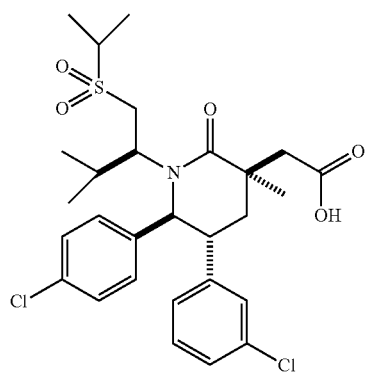

AMG 232

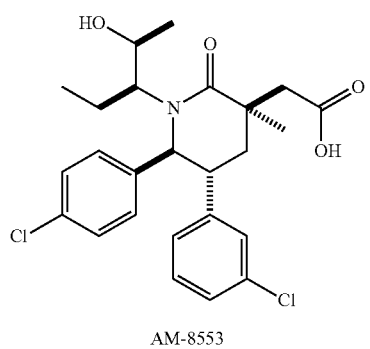

AM-8553

-continued

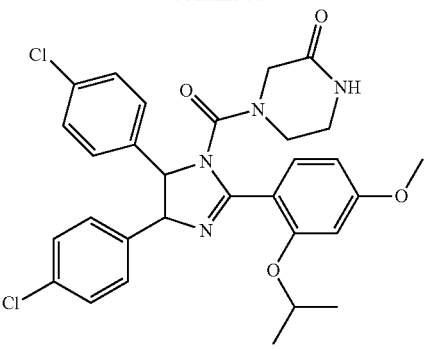

Nutlin-3

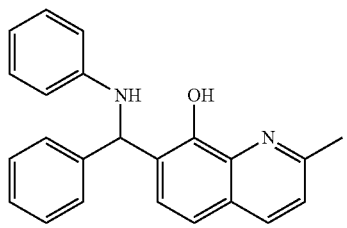

NSC 66811

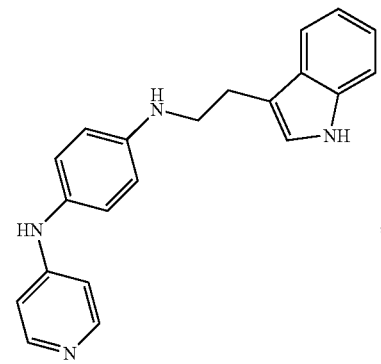

JNJ-26854165 or (S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one; or a pharmaceutically acceptable salt of any of the foregoing.

The term "pharmaceutically acceptable salts" refers to salts that retain the biological effectiveness and properties of the compound when used according to this disclosure and, which typically are not biologically or otherwise undesirable. Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, oleate, oxalate, palmitate, pamoate, phosphate/hydrogen phosphate/dihydrogen phosphate, propionate, stearate, succinate, sulfosalicylate, tartrate, tosylate, trifluoroacetate salt or the like. Inorganic acids from which salts can be derived include, for example, hydrochloric acid, hydrobromic acid, sulfuric acid, nitric acid, phosphoric acid, and the like.

In a preferred embodiment, the present disclosure relates to a Mdm2 inhibitor (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof. The Mdm2 inhibitor (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one belongs to a novel class of imidazopyrrolidinone compounds, and shows potent inhibition of the MDM2/p53 interaction (this term including in particular Hdm2/p53 interaction). In particular, this compound acts as an inhibitor of MDM2 interaction with p53 by binding to MDM2. In the most preferred embodiment, the Mdm2 inhibitor (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one is a compound of formula I, and described in Example 102 of WO2013/111105:

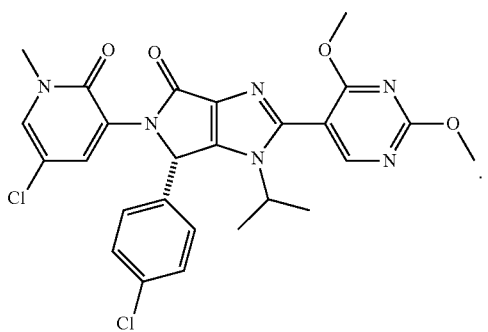

(I)

The crystalline forms of (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one are described as EX6, EX7 and EX8 in WO2013/111105. The disclosure encompasses succinic acid co-crystal of the (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one compound.

In another preferred embodiment, the present disclosure relates to a Mdm2 inhibitor (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, or a pharmaceutically acceptable salt thereof. The Mdm2 inhibitor (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one is a compound of formula II, and described in Example 106 of WO2011/076786:

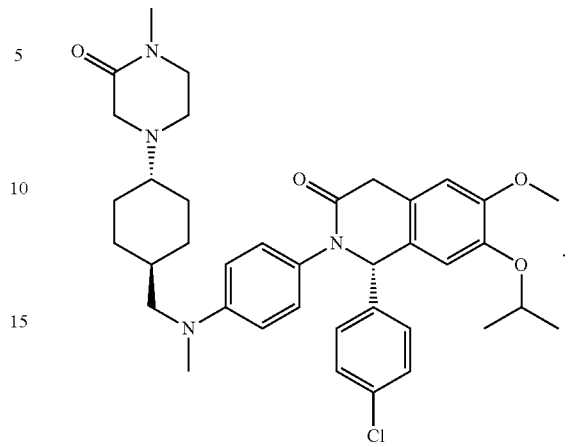

(II)

In one embodiment, the pharmaceutically acceptable salt of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one is bisulphate salt (disclosed in WO2011/076786). Crystalline form of the bisulfate salt of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one is described in WO2012/066095.

The term "administration" is also intended to include treatment regimens in which the therapeutic agents are not necessarily administered by the same route of administration or at the same time.

In one embodiment, Mdm2 inhibitor (S)-5-(5-Chloro-1-methyl-2-oxo-1,2-dihydro-pyridin-3-yl)-6-(4-chloro-phenyl)-2-(2,4-dime thoxy-pyrimidin-5-yl)-1-isopropyl-5,6-dihydro-1H-pyrrolo[3,4-d]imidazol-4-one is administered daily for the first 21 days of every 28 day cycle. In another embodiment, Mdm2 inhibitor (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one is administered daily for the first week followed by 3 weeks off treatment (drug holiday) of every 28 day cycle. In a further embodiment, Mdm2 inhibitor (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one is administered daily for the first two weeks followed by two weeks off treatment (drug holiday) of every 28 day cycle. In yet another embodiment, Mdm2 inhibitor (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one is administered daily for 3 or 5 days followed by 25 or 23 days off treatment (drug holiday), correspondingly, of every 28 day cycle. In yet another embodiment, Mdm2 inhibitor (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one is administered once every three weeks.

In one embodiment, Mdm2 inhibitor (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one is administered 3 times weekly for the first 2 weeks of every 21 day cycle (3 times for 2 week/1 week off).

The term "after the administration of said Mdm2 inhibitor" may refer to the administration of said Mdm2 inhibitor on the first day of the first cycle or any consecutive administrations of said Mdm2 inhibitor. Thus, the term "after the administration of said Mdm2 inhibitor" may refer to any administration of the Mdm2 inhibitor performed within an administration cycle.

The term "a dose of a Mdm2" inhibitor, as used herein, refers to a therapeutically effective amount of said Mdm2 inhibitor. The term "a therapeutically effective amount" of the Mdm2 inhibitor refers to an amount of the compound that will elicit the biological or medical response of a subject, for example, ameliorate symptoms, alleviate conditions, slow or delay disease progression, slow down tumor growth, or cause tumor regression, or the like. In one embodiment a therapeutically effective amount in vivo may range depending on the route of administration, between about 0.1-500 mg/kg, or between about 1-100 mg/kg.

In one embodiment, a therapeutic amount or a dose of (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one may range between 100 and 1500 mg every three weeks, particularly between 100 and 800 mg every three weeks, or between 50 and 600 mg daily, when administered per os. In a preferred embodiment, a therapeutic amount or a dose of (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one is 400 mg, more preferably 300 mg for daily administration for the first 21 days of every 28 day cycle. Alternatively, a total therapeutic amount or a total dose of (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one is 560 mg per 4 cycle (40 mg qd 2 wks on/2 wks off, or 80 mg qd 1 wk on/3 wks off). Intravenous doses would need to be lowered accordingly.

In one embodiment, a therapeutic amount or dose of(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one is between 500 and 2000 mg, particularly between 500 and 1200 mg, when administered per os. In a preferred embodiment, a therapeutic amount or dose of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one is 500 mg, more preferably 800 mg. Intravenous doses would need to be lowered accordingly.

It is understood that each therapeutic agent may be conveniently administered, for example, in one individual dosage unit or divided into multiple dosage units. It is further understood that that each therapeutic agent may be conveniently administered in doses once daily or doses up to four times a day.

In another aspect, the disclosure provides an ex vivo method for determining a toxicological effect of a Mdm2 inhibitor in a subject in vivo.

In one embodiment, the present disclosure relates to an ex vivo method for determining a toxicological effect of a Mdm2 inhibitor in a subject in vivo the method comprising the steps of:

(i) providing a pre-administration biological sample obtained from said subject prior to administration of said Mdm2 inhibitor;
(ii) measuring expression of GDF-15 in the pre-administration sample;
(iii) administering a dose of said Mdm2 inhibitor to the subject;
(iv) providing a post-administration biological sample obtained from the subject after the administration of said Mdm2 inhibitor;
(v) measuring expression of GDF-15 in the post-administration samples;
(vi) comparing expression of GDF-15 in the pre-administration sample with the level of expression of GDF-15 in the post-administration sample.

In one embodiment, the present disclosure relates to an ex vivo method for determining a toxicological effect of a Mdm2 inhibitor in a subject in vivo the method comprising the steps of:

(i) providing a pre-administration biological sample obtained from said subject prior to administration of said Mdm2 inhibitor;
(ii) measuring expression of GDF-15 in the pre-administration sample;
(iii) administering a dose of said Mdm2 inhibitor to the subject;
(iv) providing a post-administration biological sample obtained from the subject after the administration of said Mdm2 inhibitor;
(v) measuring expression of GDF-15 in the post-administration samples;
(vi) comparing expression of GDF-15 in the pre-administration sample with the level of expression of GDF-15 in the post-administration sample,
wherein the likelihood of developing thrombocytopenia in said subject in response to continuous administration of said dose of the Mdm2 inhibitor is determined.

In one embodiment, less than 50% increase of GDF-15 expression in said post-administration sample in comparison to said pre-administration sample is indicative of a decreased likelihood that the patient will develop thrombocytopenia in response to the continuous administration of said dose of the Mdm2 inhibitor. In a preferred embodiment, less than 25% increase, more preferably less than 10% of GDF-15 expression in said post-administration sample in comparison to said pre-administration sample is indicative of a decreased likelihood that the patient will develop thrombocytopenia in response to the continuous administration of said dose of the Mdm2 inhibitor. In one embodiment, at least 10% increase of GDF-15 expression in said post-administration sample in comparison to said pre-administration sample is indicative of an increased likelihood that the patient will develop thrombocytopenia in response to the continuous administration of said dose of theMdm2 inhibitor. In another embodiment, at least 25% increase of GDF-15 expression in said post-administration sample in comparison to said pre-administration sample is indicative of an increased likelihood that the patient will develop thrombocytopenia in response to the continuous administration of said dose of theMdm2 inhibitor. In a preferred embodiment, at least 50% increase of GDF-15 expression in said post-administration sample in comparison to said pre-administration sample is indicative of an increased likelihood that the patient will develop thrombocytopenia in response to the continuous administration of said dose of theMdm2 inhibitor. In yet a further embodiment, GDF-15 expression in the post-administration sample of at least 75%, at least 100% or at least 150% increase in comparison with the GDF-15 expression in the pre-administration sample is indicative of the increased likelihood for developing thrombocytopenia.

The term "biological sample", as used herein, refers to a biological specimen taken by sampling so as to be representative of any other specimen taken from the source of the specimen. In one embodiment, a biological sample is cells, tissue, blood, plasma, serum, urine, mouthwash, stool, saliva, and combination thereof. In a further embodiment, a biological sample is blood, plasma, serum, or urine. In a preferred embodiment, a biological sample is blood. In another preferred embodiment, a biological sample is serum.

The term "pre-administration biological sample", as used herein, refers to a biological sample obtained from a subject before administration of a Mdm2 inhibitor. In one embodiment, the pre-administration biological sample is obtained from a subject shortly before administration of the Mdm2 inhibitor to said subject. Alternatively, the pre-administration biological sample is obtained from a subject from about 10 min before administration of the Mdm2 inhibitor to said subject to about 7 days before administration of the Mdm2 inhibitor to said subject. In a further embodiment, the pre-administration biological sample is obtained from a subject about 10 min, or about 20 min, or about 30 min, or about 1 hour, or about 2 hours, or about 3 hours, or about 5 hours, or about 10 hours, or about 15 hours or about 1 day, or about 2 days, or about 3 days, or about 4 days, or about 5 days, or about 6 days, or about 7 days before administration of the Mdm2 inhibitor to said subject.

The term "post-administration biological sample", as used herein, refers to a biological sample obtained from a subject after administration of a Mdm2 inhibitor. In one embodiment, the post-administration sample is obtained from the subject within a timeframe of from about 30 min to about 24 hours, preferably from about 1 hour to about 12 hours, from about 2 hours to about 12 hours, about 3 hours to about 12 hours, from about 4 hours to about 8 hours, from about 5 hours to about 8 hours, about 5 hours to about 7 hours, about 6 hours to about 7 hours after administration of the Mdm2 inhibitor to said subject. In another embodiment, the post-administration sample is obtained from the subject about 30 min, about 1 hour, about 2 hours, about 3 hours, about 4 hours, about 5 hours, about 6 hours, about 7 hours, about 8 hours, about 10 hours, about 12 hours, about 24 hours after administration of the Mdm2 inhibitor. In a preferred embodiment, the post-administration sample is obtained from the subject about 3 hours after administration of the Mdm2 inhibitor. In a more preferred embodiment, the post-administration sample is obtained from the subject about 6 hours after administration of the Mdm2 inhibitor. In a further preferred embodiment, the post-administration sample is obtained from the subject about 12 hours after administration of the Mdm2 inhibitor.

The term "about" in relation to a numerical value x is optional and means, for example, x+10%.

The term "assaying" or "measuring", as used herein, refers to the act of identifying, screening, probing, determining, or measuring, which act may be performed by any conventional means. For example, a sample may be assayed for the presence of a particular marker and the level of this particular biomarker may be measured by using an ELISA assay, a Northern blot, imaging, etc. to detect whether that marker is present in the sample. The terms "assaying" and "measuring" contemplate a transformation of matter, e.g., a transformation of a biological sample, e.g., a blood sample or other tissue sample, from one state to another by means of subjecting that sample to physical testing.

In some embodiments, the nucleic acid expression level of GDF-15 is measured. In some embodiments, the nucleic acid expression level of GDF-15 is measured by hybridization. In some embodiments, the nucleic acid expression level of GDF-15 is measured by amplification. In further embodiments, the amplification method for measuring the nucleic acid expression level of GDF-15 is RT-PCT amplification. In yet further embodiments, the method used for measuring the nucleic acid expression level of GDF-15 is selected from the group consisting of Nucleic Acid Sequence Based Amplification (NASBA), Transcription Mediated Amplification (TMA), Quantitative PCR (qPCR), Real-Time PCT, Loop-Mediated Isothermal Amplification (LAMP), TaqMan, Invader, InvaderPlus, Rolling Circle, Strand Displacement Amplification (SDA), Q-Beta-Replicase, Helicase Dependent Amplification (HAD), Branched DNA, Hydrolysis FRET probes, Ligase Chain Reaction (LCR), degenerate oligonucleotide primed PCR, or other methods known to those skilled in the art. In one embodiment, GDF-15 expression is assayed by measurement of GDF-15 gene transcription. In one embodiment, GDF-15 gene expression can be assayed by means of an oligonucleotide probe that specifically hybridizes to a region of a nucleic acid coding for GDF-15.

In some embodiments the protein expression level of GDF-15 is measured. In some embodiments the protein expression level of GDF-15 is measured by performing an immune assay using one or more antibodies that specifically bind GDF-15 protein or fragment thereof, in particular by performing ELISA. In some embodiments the protein expression level of GDF-15 is measured by performing 2D-gel electrophoresis. In a preferred embodiment, GDF-15 expression is assayed by measurement of GDF-15 protein level in a biological sample. GDF-15 protein level can be assayed by means of an antibody that binds to GDF-15 protein, or fragment thereof.

In another aspect, the disclosure provides a Mdm2 inhibitor for use in the treatment of cancer in a subject, comprising
  (i) measuring GDF-15 expression in a pre-administration biological sample obtained from said subject before a dose of the Mdm2 inhibitor has been administered to said subject;
  (ii) measuring GDF-15 expression in a post-administration biological sample obtained from said subject after a dose of the Mdm2 inhibitor has been administered to said subject;
  (iii) comparing the GDF-15 expression in the pre-administration sample with the GDF-15 expression in the post-administration sample; and
  (iv) altering the treatment of said subject, when the GDF-15 expression in the post-administration sample is at least 25%, preferably at least 50% higher in comparison with the GDF-15 expression in the pre-administration sample; or
  (v) making no changes to the administration regimen of said Mdm2 inhibitor to said subject, when the level of GDF-15 expression in the post-administration sample is less than 50%, preferably less than 25% higher in comparison with the GDF-15 expression in the pre-administration sample.

In one embodiment, GDF-15 expression in the post-administration sample of at least 25%, preferably at least 50% increase in comparison with the GDF-15 expression in the pre-administration sample is indicative of the increased likelihood for developing thrombocytopenia.

In a further embodiment, GDF-15 expression in the post-administration sample of at least 75%, at least 100% or at least 150%-increase in comparison with the GDF-15 expression in the pre-administration sample is indicative of the increased likelihood for developing thrombocytopenia.

In one embodiment, the disclosure provides a Mdm2 inhibitor for use in the treatment of cancer in a subject, comprising
  (i) measuring GDF-15 expression in a pre-administration biological sample obtained from said subject before a dose of the Mdm2 inhibitor has been administered to said subject;
  (ii) measuring GDF-15 expression in a post-administration biological sample obtained from said subject after a dose of the Mdm2 inhibitor has been administered to said subject;
  (iii) comparing the GDF-15 expression in the pre-administration sample with the GDF-15 expression in the post-administration sample; and
  (iv) altering the treatment of said subject, when the GDF-15 expression in the post-administration sample is at least 75%, preferably at least 100%, more preferably at least 150% higher in comparison with the GDF-15 expression in the pre-administration sample; or
  (v) making no changes to the administration regimen of said Mdm2 inhibitor to said subject, when the level of GDF-15 expression in the post-administration sample is less than 150%, preferably less than 100%, more preferably less than 75% higher in comparison with the GDF-15 expression in the pre-administration sample.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "cancer" refers to cancer diseases including, for example, breast, lung, pancreas, ovary, central nervous system (CNS), endometrium, stomach, large intestine, colon, esophagus, bone, urinary tract, hematopoietic, lymphoid, liver, skin, melanoma, kidney, soft tissue sarcoma and pleura.

In one embodiment, alteration of the treatment comprises alteration of the administration regimen of said Mdm2 inhibitor to the subject and/or administering the means for reducing the Mdm2 inhibitor effect on thrombocytes. In a further embodiment, the alteration of the treatment comprises a reduction of a dose of said Mdm2 inhibitor, and/or reduction of a frequency of administration of said Mdm2 inhibitor and/or drug holiday and/or complete discontinuation of the treatment. In a preferred embodiment, the means for reducing the Mdm2 inhibitor effect on thrombocytes of the treatment comprise platelet transfusion. In a further preferred embodiment, the the means for reducing the Mdm2 inhibitor effect on thrombocytes comprise administration of a thrombopoietin receptor agonist, and wherein said thrombopoietin receptor agonist is eltrombopag. Eltrombopag—(rINN, codenamed SB-497115-GR, trade names: Promacta, Revolade) is a small molecule agonist of the c-mpl (TpoR) receptor, which is the physiological target of the hormone thrombopoietin.

In another embodiment, the alteration of the treatment comprises a discontinuation of the treatment with said Mdm2 inhibitor. In yet another embodiment, the treatment alteration comprises a drug holiday. The term "drug holiday", as used herein, sometimes also called a drug vacation, medication vacation, structured treatment interruption or strategic treatment interruption, refers to a discontinuation of the treatment for a period of time; anywhere from a few days to a few months or a few years. In one embodiment, the drug holiday is a discontinuation of the treatment with the Mdm2 inhibitor for a period of 1 week, 2 weeks, 3 weeks or 4 weeks.

In one embodiment, a biological sample is cells, tissue, blood, plasma, serum, urine, mouthwash, stool, saliva, and combination thereof. In a further embodiment, a biological sample is blood, plasma, serum, or urine. In a preferred embodiment, a biological sample is blood.

In a further aspect, the present disclosure relates to a kit for use in predicting the likelihood that a patient having cancer will develop thrombocytopenia in response to a continuous treatment with a Mdm2 inhibitor comprising
  (i) at least one probe capable of detecting the GDF-15 expression; and
  (ii) instructions for using the probe to assay a biological sample obtained from the patient for the GDF-15 expression, wherein
    (a) at least 25% increase, more preferably at least 50% increase of GDF-15 expression after administration of said dose of said Mdm2 inhibitor to said patient is indicative of an increased likelihood that said patient will develop thrombocytopenia in response to the continuous treatment with said dose of the Mdm2 inhibitor, and
    (b) less than 50% increase, more preferably less than 25% increase in GDF-15 expression after administration of said dose of said Mdm2 inhibitor to said patient is indicative of a decreased likelihood that said patient will develop thrombocytopenia in response to the continuous treatment with said dose of the Mdm2 inhibitor.

As used herein, "predicting" indicates that the methods described herein provide information to enable a health care provider to determine the likelihood that an individual subjected to a treatment will develop with a higher likelihood thrombocytopenia. It does not refer to the ability to predict response with 100% accuracy. Instead, the skilled artisan will understand that it refers to an increased probability.

In one embodiment, the kit comprises the probe, which is an oligonucleotide that specifically hybridizes to a region of a nucleic acid coding for GDF-15, or an antibody that binds to GDF-15 protein.

In yet a further aspect, the present disclosure relates to a kit for use in treating a patient having cancer comprising:
  (i) a therapeutically effective amount of a Mdm2 inhibitor;
  (ii) at least one probe capable of detecting the GDF-15 expression;
  (iii) instructions for using the probe to assay a biological sample obtained from the patient for the GDF-15 expression; and
  (iv) instructions for applying the means to the patient if the biological sample obtained from the patient after the therapeutically effective amount of the Mdm2 inhibitor has been administered to the patient has at least 25% increased, more preferably at least 50% increased GDF-15 expression in comparison to the level of GDF-15 expression in a pre-administration sample obtained from said patient.

In one embodiment, the kit comprises the probe, which is an oligonucleotide that specifically hybridizes to a region of a nucleic acid coding for GDF-15, or an antibody that binds to GDF-15 protein.

Where the aspects of the present invention concern a medical use or a method of treatment comprising an active pharmaceutical ingredient (API, e.g. Mdm2 inhibitor, thrombopoietin receptor agonist) and an indication (e.g. cancer, thrombocytopenia), those aspects may be worded in the following alterative formats:

[API] for use in the treatment of [INDICATION].

Method for treatment of [INDICATION] in human patients in need of such treatment which comprises administering an effective amount of [API].

[API] for the preparation of a medicament for the treatment of [INDICATION].

A medicament for the treatment of [INDICATION] comprising [API].

It was further surprisingly found that the GDF-15 expression is not only indicative for the likelihood that a patient having cancer will develop thrombocytopenia but also indicative for the likelihood that a patient having cancer will develop neutrocytopenia, i.e. an abnormal low concentration of neutrophils, e.g. a neutrophil count of less than $1.5 \times 10^9$ cells/L [see Hsieh M M, et al. (April 2007): "Prevalence of neutropenia in the U.S. population: age, sex, smoking status, and ethnic differences". Ann. Intern. Med. 146 (7): 486-92].

Based on this surprising finding, the present invention further provides all the aspects as described herein with respect to platelets/platelet counts/thrombocytopenia also in the corresponding alternative version with respect to neutrophils/neutrophil counts/neutropenia.

The following Examples illustrates the disclosure described above, but is not, however, intended to limit the scope of the disclosure in any way. Other test models known as such to the person skilled in the pertinent art can also determine the beneficial effects of the claimed disclosure.

EXAMPLES

Example 1

Method:

Patients were treated with (5)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (Compound A). Dose range was from 10 to 500 mg three times a week (3QW) with continuous or 2 week on 1 week off dosing regimen. Serum samples were collected from each subject at pre-dose and from 0.5 to 6 h post-dose on the first treatment day.

The serum level of GDF-15 expression was measured using enzyme-linked immunosorbent assay (ELISA; R&D Systems kit DGD150).

Clinical data (including platelet counts) were collected from all patients during the course of the treatment period.

Maximum observation period was 448 days on available platelet data.

Figure 1:
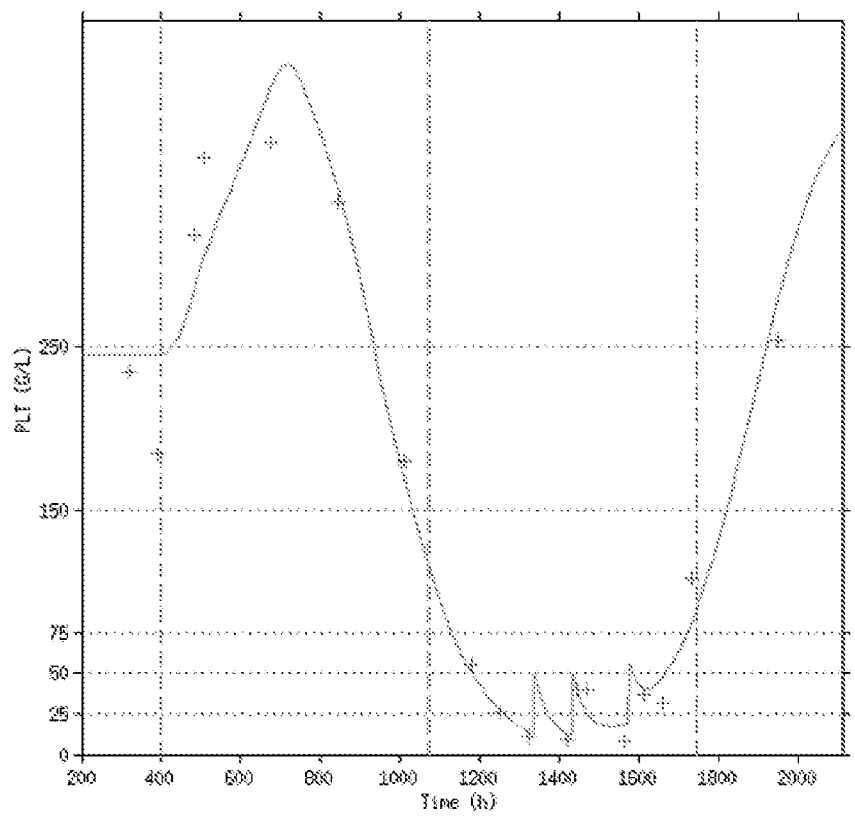
FIG. 1 Observed and individually fitted time profile of the platelet count of a patient treated with (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one on a continuous three times weekly oral dosing regimen. First administration is at time 400 h on this graph. Patient did undergo 3 platelets transfusion events.
Figure 2:
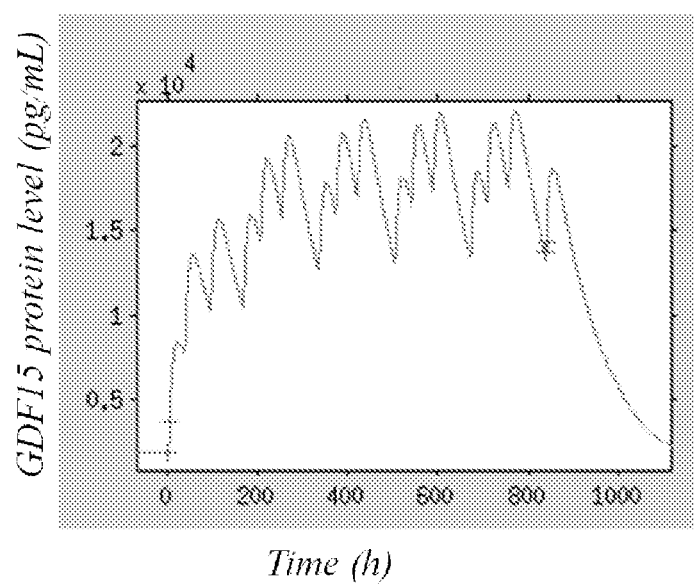
FIG. 2 Observed and individually fitted time profile of the GDF-15 protein level of a patient treated with (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one on a 3qw continuous dosing regimen.

Results:

FIG. 1 represents, on the example of one patient, the typical observed and individually predicted time profile of the platelet count of a patient treated with (S)-1-(4-Chlorophenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one on a 3QW continuous dosing regimen. The model also integrates any dose interruptions after 4 weeks of dosing, as well as the impact of PLT transfusion events. On the graph represented on FIG. 1, the first administration is at time 400 h. FIG. 2 represents, on the example of the same patient represented in FIG. 1, observed and individually fitted time profile of the GDF-15 protein level of the patient treated with (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one on a 3qw continuous dosing regimen.

Figure 3:
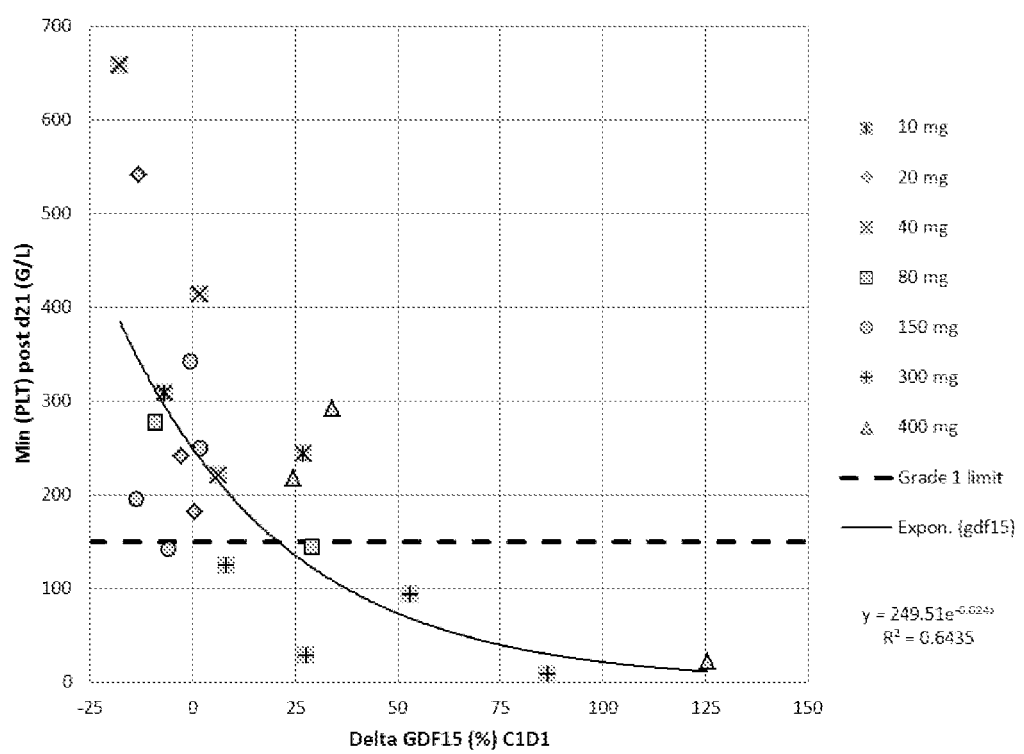
FIG. 3 A preliminary data analysis of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one effect on GDF-15 and platelet counts for 21 patients treated on a continuous three times weekly oral administration of (S)-1-

A preliminary data analysis of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one effect on GDF-15 and platelet counts for 21 patients treated on a continuous three times weekly oral administration of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one was conducted. The conducted data analysis is represented in a plot on FIG. 3. In this plot, each point represents an individual patient. X coordinate being the cycle 1 day 1 GDF-15 increase in percentage change (%) from baseline. Y coordinate represents the lowest observed platelet count for the same patient during the course of the treatment. As shown on this plot, an increase in GDF-15 levels by more than 25% from baseline is associated with a higher occurrence of platelet counts dropping below 150 G/L (grade 1 thrombocytopenia CTCAE V4).

Example 2

Method:

This approach allows for data analysis with heterogeneity in dosing regimen, and sampling time for GDF-15. A PK/PD model describing the complete time course of drug concentration, GDF-15 levels and platelets (PLT) was developed. Because of the high inter-individual variability, all modeling analysis was done applying nonlinear mixed effects modeling.

Relationship between drug concentration (PK) and GDF-15 kinetics was described by an indirect response model with stimulation of production (type III, Br J Clin Pharmacol 1998; 45: 229-239). By applying this approach, individual drug potency on GDF-15 $slG_i$ production was estimated.

Relationship between PK and PLT time course was described by a PKPD model mimicking hematopoiesis (Friberg L. et al. J Clin Oncol. 2002 Dec. 15; 20(24): 4713-21.). This model includes local and systemic regulations of PLT production and takes into account PLT transfusion events as infusions in the PLT circulating compartment. Individual drug potency on immature hematopoietic cells $slP_i$ was estimated.

Data Used for the PKPD Modeling:

Patients were treated with (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one. A total of 45 subjects were used for the PKPD modeling of thrombocytopenia. Dose range was from 10 to 500 mg 3 times a week (3QW) with continuous or 2 W on 1 W off dosing regimen. Serum samples were collected from each subject at pre-dose and from 0.5 to 8 h post-dose on C1D1, C1D8 and C2D1. The serum level of GDF-15 protein levels was measured using enzyme-linked immunosorbent assay (ELISA; R&D Systems kit DGD150). Clinical data (including platelet counts) were collected from all patients during the course of the treatment period. Maximum observation period was 448 days on available platelet data.

Results:

PKPD model is described in FIGS. 4 and 5 and model code reported in appendix A1.

FIG. 5 represents schematic of the PKPD model used to describe GDF-15 kinetics. Tlag and ka are delay and first order drug absorption rate parameters respectively. k12 and k21 inter-compartimental rates, ke elimination rate, Vm and km Michaelis Menten elimination parameters. kout is the turnover rate of the indirect response model and kin the zero order production. V is the apparent volume of the central compartment and Qc/V the drug concentration.

FIG. 4 represents PKPD model used to describe platelets kinetics. MMT is the mean maturation time, E([C]) is a drug effect function of drug concentration. Circ. compartment represents circulating platelets, Prol.—proliferative immature cells and A2, A3, A4—maturation compartments. Link between estimated drug potencies on GDF-15 and bone marrow was first explored by plotting $slG_i$ (individual drug potency on GDF-15 $slG_i$ production) versus $slP_i$ (individual drug potency on immature hematopoietic cells).

FIG. 6 illustrates a preliminary result exploring the link between the 2 parameters, namely the link between ndividual drug potency on GDF-15 (slGi) production against the individual drug potency on immature hematopoietic cells (slPi). This analysis was done with data derived from 45 patients.

Below in Appendix A1, an exemplary depiction of a PKPD model is presented. All modeling was performed using the nonlinear mixed effects modeling software MONOLIX (Ver. 4.3.2) (as described for example in "Estimation of population pharmacokinetic parameters of saquinavir in HIV patients with the MONOLIX software. J Pharmacokinet Pharmacodyn. 2007 April; 34(2):229-49. Lavielle M, Mentré F." or http://www.lixoft.eu/)

APPENDIX A1

| PKPD model code in MLXTRAN language found under MONOLIX 4.3.2 |
|---|
| DESCRIPTION: PKPD model PK, PLT and GDF-15<br>INPUT:<br>parameter = {ka, V, ke, Vm, PKlag, PLTz, MMTP, alp, SEP, slP, Sg, sPW,<br>lPW, gdfZ, kinG, koutG, km, k12, k21}<br>PK:<br>compartment(cmt=1, amount=Ag)<br>compartment(cmt=2 , amount=P5)<br>iv(adm=1,  cmt=1, Tlag = PKlag)<br>Tk0 = 0.5<br>oral(adm=2, cmt=2, Tk0, p=alp)<br>EQUATION:<br>hv=1<br>odeType = stiff<br>t0 = 0<br>; PK model<br>Cc              = max(1e−16,Ac/V)<br>ddt_Ag    = −ka*Ag<br>ddt_Ac    = ka*Ag − ke*Ac −k12*Ac+k21*Ad   −(Vm^hv)/((km*V)^hv+Ac^hv)*Ac<br>ddt_Ad    = k12*Ac  −  k21*Ad<br>; PLT MODEL<br>ktrP         = 4/MMTP<br>phiP        = ktrP<br>EP          = slP * Cc ^SEP<br>sfbkP = (PLTz/P5)^sPW<br>lfbkP   = (PLTz*phiP/ktrP/P1)^lPW<br>P1_0 = PLTz*phiP/ktrP<br>P2_0 = PLTz*phiP/ktrP<br>P3_0 = PLTz*phiP/ktrP<br>P4_0 = PLTz*phiP/ktrP<br>P5_0 = PLTz<br>ddt_P1 = ktrP*(sfbkP−EP)*P1    − ktrP*P1<br>ddt_P2 = ktrP*lfbkP *P1         − ktrP*P2<br>ddt_P3 = ktrP*lfbkP *P2         − ktrP*P3<br>ddt_P4 = ktrP*lfbkP *P3         − ktrP*P4<br>ddt_P5 = ktrP*lfbkP *P4         − phiP*P5<br>;GDF-15 model<br>Egdf      = Sg*Cc<br>kin         = kinG;koutG*gdfZ<br>gdf_0    = gdfZ<br>ddt_gdf  = kin*(1+Egdf) − koutG*gdf<br>OUTPUT:<br>    output = {Cc, P5, gdf} |

Example 3

As described above, a PKPD thrombocytopenia model was used to establish the link between Compound A drug potency on GDF-15 and on bone marrow. This approach further verified the importance of GDF-15 as a biomarker to improve the prediction of delayed drug-induced thrombocytopenia early enough to properly apply measures to minimize thrombocytopenia or prevent it altogether. This data also supports the notion that a similar correlation between GDF-15 and drug-induced thrombocytopenia would exist with other MDM2 inhibitors, including (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one. Taking the learning from Compound A, a similar approach described here could be used as a guidance which could be followed for other MDM2 inhibitors. For example, if another Mdm2 inhibitor is used, the correlation between a relative increase of the level of GDF-15 expression in a subject after administration of a dose of a Mdm2 inhibitor (i.e. GDF-15 expression in a post-administration sample obtained from a subject) in comparison to a baseline level of expression of GDF-15 in the same subject (i.e. GDF-15 expression in a pre-administration sample from the subject) and the likelihood of developing thrombocytopenia in the same subject could be arrived at by completing the following steps:

1) providing a pre-administration biological sample obtained from a subject prior to administration of said Mdm2 inhibitor;
2) measuring expression of GDF-15 in the pre-administration sample;
3) administering a dose of said another Mdm2 inhibitor to the subject;
4) providing a post-administration biological sample obtained from the subject after the administration of said Mdm2 inhibitor;
5) measuring expression of GDF-15 in the post-administration samples;
6) Selecting a PK model specific for said Mdm2 inhibitor and which describes the individual PK profile;
7) Establishing the PKPD relationship by describing the effect of said Mdm2 inhibitor on the time-course of platelet (PLT) counts using a semi-mechanistic model with a chain of five compartments reproducing the hematopoietic maturation process (as was described for Compound A in Appendix A1), while keeping some PD parameters in the model such as baseline of platelets and their maturation time, and the feedback parameters the same as used in the Compound A model. Drug potency will be specific for the new drug and is estimated from the model. The Mdm2 inhibitor dosing regimen is considered in the PKPD model.
8) Establishing the PKPD relationship for GDF-15. Structure and physiological parameters (baseline of GDF-15, turnover rate) should be the kept the same as in the Compound A model. Drug potency on GDF-15 production and on platelet production are read from the model as fixed values, which are specific to the given Mdm2i and independent on the dosing regimen.
9) Determining the correlation between drug potency on platelet production and GDF-15 individual parameter to establish the level of GDF-15 expression (early) increase required to cause predicted delayed thrombocytopenia. In addition, drug potency on GDF-15 can be considered in the drug action on PLT production in order to reduce the inter-individual variability of the PLT drug potency.

Ultimately, the PKPD model established should be used to define appropriate dose reduction or any measure to prevent thrombocytopenia.

Every expert in the field would be aware of a general guidance on preparing a PK and PKPD model, for example with respect to minimum number of data points and thus patients that would be required in order to arrive at the satisfactory model, or how the required numbers of data points (i.e. patients) may depend based on variability of the data set, or drug toxicity (i.e. may depend on the level of changes in PLT numbers or differential GDF-15 expression). The PK model selected should be the one that best describes the PK profile of the respective Mdm2 inhibitor. It is in a general purview of a skilled person how to prepare a PK model for a given pharmaceutical compound, in the present case a Mdm2 inhibitor, particularly (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a salt thereof. A skilled person can also refer to general principles of PK modeling to "Pharmacokinetic and Pharmacodynamic Data Analysis: Concepts and Applications", Fourth Edition, 2007, Swedish Pharmaceutical Press, by Johan Gabrielsson and Daniel Weiner.

Example 4

Maximum change of platelet count (FIG. 7) and neutrophil count (FIG. 8) and the GDF-15 values were determined for patients with solid tumors receiving compound of formula I, i.e. (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, on the first day of a three week cycle (herein also referred to as regimen 1A or q3w) in doses of 12.5 mg (A), 25 mg (B), 50 mg (C), 100 mg (D), 200 mg (E), 250 mg (F), 350 mg(G) or on the first and eighth day of a 4 week cycle (herein also referred to as regimen 1B) in a dose of 120 mg (I). The left graphs show the maximum platelet count change vs. GDF-15 fold change, the GDF-15 being measured on day 1 of the first cycle (C1D1). The right graphs show the maximum platelet count change vs. GDF-15 fold change.

The platelet/neutrophil count was determined before receipt of first dose (baseline) and on day 1, 7 and 15 of the first and second cycle for regimen 1A (A-G) or on day 1, 8, 14, 22 of the first and second cycle for regimen 1B (I) and the maximum platelet change value in comparison to the baseline was selected. The "Change of platelet/neutrophile counts" value is calculated as post-baseline value minus baseline value and given in number of platelets/neutrophils per microliter of blood.

The GDF-15 was determined before receipt of first dose (baseline, C1D1 pre-dose) and 24 h after first dose on the first day of first cycle (C1D1 24 h post-dose) and 24 h after the dose of first day of second cycle (C2D1 24 h post-dose) for regimen 1A (A-G) and regimen 1B (I). For regimen 1B one further GDF-15 value was determined on 8 h after the dose on day 8 of the first cycle (C1D8 8 h post-dose). The "GDF-15 C1D1 fold change" is defined as C1D1 24 post-dose/C1D1 pre-dose. The "GDF-15 max fold change" is defined as the maximum value of the post-dose values divided by the C1D1 pre-dose value.

This demonstrates that the increase of the biomarker GDF-15 correlates with a decrease of the platelet and neutrophil count during the treatment with compound of formula I. This correlation was observed already for the GDF-15 C1D1 values as being determined 24 h after the first dose of the compound of formula I (see left graphs of FIG. 7 and FIG. 8). Therefore, an increase of the GDF-15 values in the early phase of a treatment with a Mdm2 inhibitor is indicative for a decrease of the platelet and neutrophil counts during the said treatment.

The invention claimed is:

1. An ex vivo method for determining the likelihood of developing thrombocytopenia in a subject in vivo, in response to continuous administration of a murine double minute 2 (Mdm2 inhibitor), the method comprising the steps of:
   (i) providing a pre-administration biological sample obtained from said subject prior to administration of an Mdm2 inhibitor;
   (ii) measuring expression of Growth differentiation factor 15 (GDF-15) in the pre-administration sample;
   (iii) administering a continuous dose of said Mdm2 inhibitor to the subject;

(iv) providing a post-administration biological sample obtained from the subject after the administration of said Mdm2 inhibitor;
(v) measuring expression of GDF-15 in the post-administration samples;
(vi) comparing expression of GDF-15 in the pre-administration sample with the level of expression of GDF-15 in the post-administration sample;
(vii) altering the continuous administration of the dose of said Mdm2 inhibitor to said subject when the GDF-15 expression in the post-administration sample is at least 25% higher in comparison with the GDF-15 expression in the pre-administration sample, wherein said alteration of dose of Mdm2 inhibitor is discontinuation of the continuous dose of said Mdm2 inhibitor or reduction of the continuous dose of said Mdm2 inhibitor; and
(viii) treating said subject, wherein said treatment is selected from administration of thrombopoietin, administration of a thrombopoietin receptor agonist, a platelet transfusion or a drug holiday.

2. The method of claim 1, wherein less than 25% increase of GDF-15 expression in said post-administration sample in comparison to said pre-administration sample is indicative of a decreased likelihood that the patient will develop thrombocytopenia in response to the continuous administration of said dose of the Mdm2 inhibitor.

3. The method of claim 1, wherein at least 25% increase of GDF-15 expression in said post-administration sample in comparison to said pre-administration sample is indicative of an increased likelihood that the patient will develop thrombocytopenia in response to the continuous administration of said dose of the Mdm2 inhibitor.

4. The method of claim 1, wherein said post-administration sample is obtained within a timeframe from about 30 min to about 24 hours, from about 1 hour to about 12 hours, from about 2 hours to about 12 hours, about 3 hours to about 12 hours, from about 4 hours to about 8 hours, from about 5 hours to about 8 hours, about 5 hours to about 7 hours, about 6 hours to about 7 hours after administration of the Mdm2 inhibitor.

5. The method of claim 4, wherein said post-administration sample is obtained about 30 min, about 1 hour, about 2 hours, about 3 hours, about 4 hours, about 5 hours, about 6 hours, about 7 hours, about 8 hours, about 10 hours, about 12 hours, about 24 hours after administration of the Mdm2 inhibitor.

6. The method according to claim 1, wherein said GDF-15 expression is assayed by measurement of GDF-15 gene transcription.

7. The method according to claim 6, wherein said GDF-15 gene expression is assayed by means of an oligonucleotide probe that specifically hybridizes to a region of a nucleic acid coding for GDF-15.

8. The method according to claim 1, wherein said GDF-15 expression is assayed by measurement of GDF-15 protein level in a biological sample.

9. The method according to claim 8, wherein said GDF-15 protein level is assayed by means of an antibody that binds to GDF-15 protein.

10. The method according to claim 8, wherein the biological sample is blood, plasma, serum or urine.

11. The method according to claim 1, wherein GDF-15 expression in the post-administration sample of at least 75%, 100% or 150% increase in comparison with the GDF-15 expression in the pre-administration sample is indicative of the increased likelihood for developing thrombocytopenia.

12. The method according to claim 1, wherein said Mdm2 inhibitor is selected from the group consisting of:

(S)-1-(4-Chloro-phenyl)-7-isopropoxy-6-methoxy-2-(4-{methyl-[4-(3-oxo-piperazin-1-yl)-trans-cyclohexylmethyl]-amino}-phenyl)-1,4-dihydro-2H-isoquinolin-3-one;

(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one;

(S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one;

(S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one;

(S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one;

1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one;

(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;

(S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

(S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;

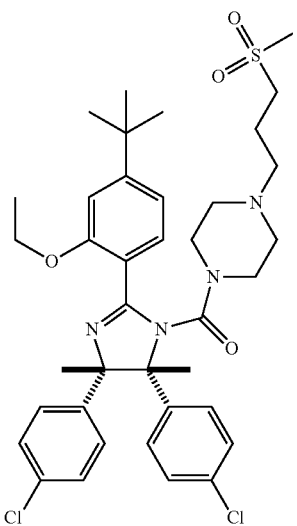

RG7112

-continued

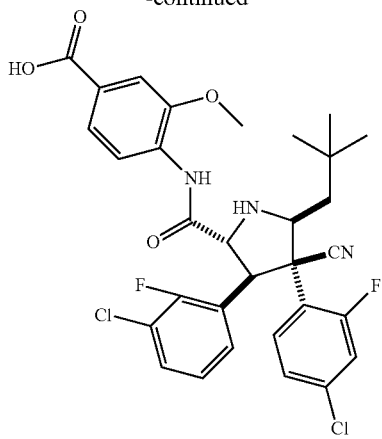

RG7388

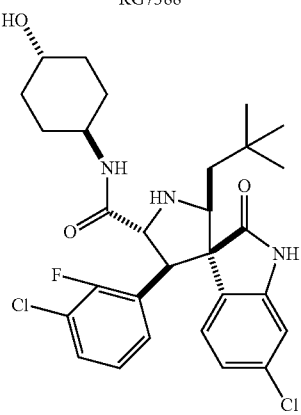

SAR299155

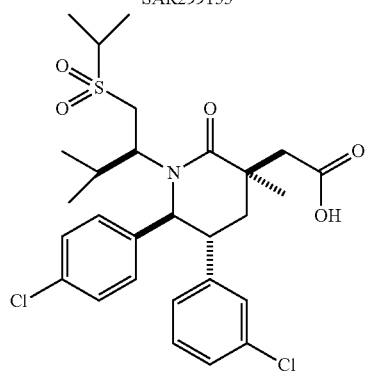

AMG 232

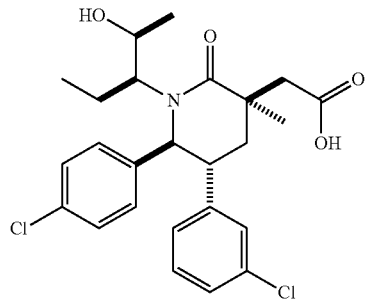

AM-8553

-continued

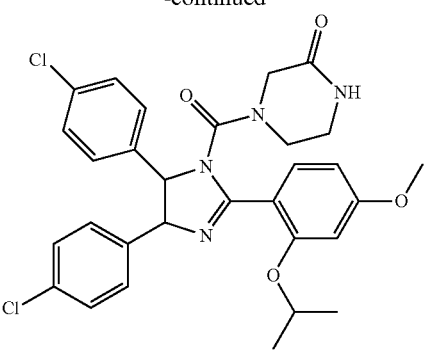

Nutlin-3

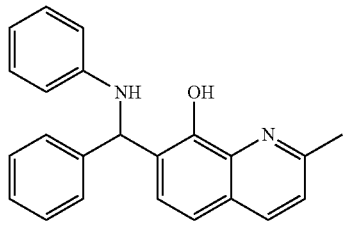

NSC 66811

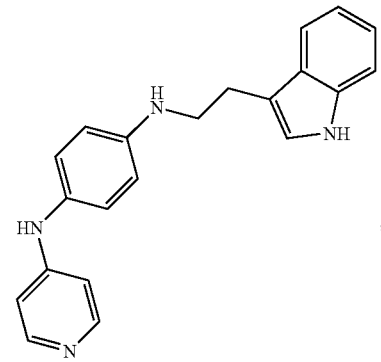

JNJ-26854165 and (S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one; or a pharmaceutically acceptable salt of any of the foregoing.

13. The method according to claim 1, wherein said Mdm2 inhibitor is (S)-5-(5-Chloro-1-methyl-2-oxo-1,2-dihydropyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof.

14. The method according to claim 1, wherein said Mdm2 inhibitor is (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, or a pharmaceutically acceptable salt thereof.

* * * * *